US012728011B2

(12) United States Patent
Ball et al.

(10) Patent No.: US 12,728,011 B2
(45) Date of Patent: Sep. 8, 2026

(54) SHOULDER IMPLANTS AND METHODS OF USE AND ASSEMBLY

(71) Applicant: STRYKER EUROPEAN OPERATIONS LIMITED, County Cork (IE)

(72) Inventors: Robert J. Ball, West Olive, MI (US); William J. Slone, Silver Lake, IN (US)

(73) Assignee: Stryker European Operations Limited (IE)

( * ) Notice: Subject to any disclaimer, the term of this patent is extended or adjusted under 35 U.S.C. 154(b) by 713 days.

(21) Appl. No.: 18/055,982

(22) Filed: Nov. 16, 2022

(65) Prior Publication Data

US 2023/0079674 A1 Mar. 16, 2023

Related U.S. Application Data

(62) Division of application No. 16/756,429, filed as application No. PCT/US2018/055490 on Oct. 11, 2018, now Pat. No. 11,564,802.

(Continued)

(51) Int. Cl.
*A61F 2/40* (2006.01)
*A61F 2/30* (2006.01)

(52) U.S. Cl.
CPC ...... *A61F 2/40* (2013.01); *A61F 2002/30332* (2013.01); *A61F 2002/30433* (2013.01); *A61F 2002/30507* (2013.01); *A61F 2002/30566* (2013.01); *A61F 2002/4022* (2013.01); *A61F 2002/4077* (2013.01)

(58) Field of Classification Search
CPC ............................................... A61F 2/40–4081
See application file for complete search history.

(56) References Cited

U.S. PATENT DOCUMENTS 4,550,450 A 11/1985 Kinnett
4,725,280 A 2/1988 Laure
(Continued)

FOREIGN PATENT DOCUMENTS

AU 2012204090 A1 8/2012
CN 111818880 B 3/2025
(Continued)

OTHER PUBLICATIONS

Extended European Search Report issued in connection with European Patent Application No. 22846386.5, Mar. 12, 2025, 7 pages.
(Continued)

*Primary Examiner* — Marcia L Watkins
(74) *Attorney, Agent, or Firm* — DUANE MORRIS LLP

(57) ABSTRACT

An implant is disclosed that a base member configured to be secured in bone, the base member includes a plate portion, an articulating member, and a coupling portion for securing the base member to the articulating member. A stem extends from the plate portion, where the stem is positioned offset from a center of the plate portion. The coupling portion includes a first fixation component, and a second fixation component including an opening for receiving the first fixation component, where the first fixation component is coupled to the articulating member and the second fixation component is coupled to the base member.

12 Claims, 24 Drawing Sheets

Related U.S. Application Data

(60) Provisional application No. 62/572,920, filed on Oct. 16, 2017.

(56) References Cited

U.S. PATENT DOCUMENTS 4,919,670 A 4/1990 Dale et al.
4,986,833 A 1/1991 Worland
4,990,161 A 2/1991 Kampner
5,032,132 A 7/1991 Matsen, III et al.
5,033,036 A 7/1991 Ohmori et al.
5,080,673 A 1/1992 Burkhead et al.
5,108,446 A 4/1992 Wagner et al.
5,458,637 A 10/1995 Hayes
5,489,309 A 2/1996 Lackey et al.
5,489,311 A 2/1996 Cipolletti
5,531,973 A 7/1996 Sarv
5,662,657 A 9/1997 Carn
5,702,447 A 12/1997 Walch et al.
5,800,551 A 9/1998 Williamson et al.
5,954,722 A 9/1999 Bono
6,102,951 A 8/2000 Sutter et al.
6,102,954 A 8/2000 Albrektsson et al.
6,171,342 B1 1/2001 O'Neil et al.
6,228,119 B1 5/2001 Ondrla et al.
6,228,120 B1 5/2001 Leonard et al.
6,406,495 B1 6/2002 Schoch
6,508,841 B2 1/2003 Martin et al.
6,514,287 B2 2/2003 Ondrla et al.
6,673,115 B2 1/2004 Resch et al.
6,679,916 B1 1/2004 Frankle et al.
6,699,289 B2 3/2004 Iannotti et al.
6,719,799 B1 * 4/2004 Kropf .................. A61F 2/4014 623/19.12
6,761,740 B2 7/2004 Tornier
6,783,549 B1 8/2004 Stone et al.
6,790,234 B1 9/2004 Frankle et al.
6,860,903 B2 3/2005 Mears et al.
6,911,047 B2 6/2005 Rockwood, Jr. et al.
6,953,478 B2 10/2005 Bouttens et al.
6,969,406 B2 11/2005 Tornier
7,160,328 B2 1/2007 Rockwood, Jr. et al.
7,169,184 B2 1/2007 Dalla Pria
7,175,663 B1 2/2007 Stone
7,175,665 B2 2/2007 German et al.
7,204,854 B2 4/2007 Guederian et al.
7,316,715 B2 1/2008 Plaskon
7,462,197 B2 12/2008 Tornier et al.
7,462,199 B2 12/2008 Justin et al.
7,604,665 B2 10/2009 Iannotti et al.
7,608,109 B2 10/2009 Dalla Pria
7,611,539 B2 11/2009 Bouttens et al.
7,621,961 B2 11/2009 Stone
7,637,928 B2 12/2009 Fernandez
7,648,530 B2 1/2010 Habermeyer et al.
7,666,522 B2 2/2010 Justin et al.
7,753,959 B2 7/2010 Berelsman et al.
7,766,969 B2 8/2010 Justin et al.
7,854,768 B2 12/2010 Wiley et al.
7,883,653 B2 2/2011 Smith et al.
7,892,287 B2 2/2011 Deffenbaugh
7,922,769 B2 4/2011 Deffenbaugh et al.
7,927,335 B2 4/2011 Deffenbaugh et al.
7,993,408 B2 8/2011 Meridew et al.
8,007,523 B2 8/2011 Wagner et al.
8,048,161 B2 11/2011 Guederian et al.
8,052,758 B1 * 11/2011 Winslow ............... A61F 2/4014 623/22.42
8,062,376 B2 11/2011 Shultz et al.
8,070,820 B2 12/2011 Winslow et al.
8,092,545 B2 1/2012 Coon et al.
8,177,849 B2 * 5/2012 Meyers ................ A61F 2/3607 623/20.32
8,206,453 B2 6/2012 William et al.
8,231,683 B2 7/2012 Lappin et al.
8,241,365 B2 8/2012 Williams, Jr. et al.
8,287,600 B2 10/2012 Angibaud
8,308,807 B2 11/2012 Seebeck et al.
8,357,201 B2 1/2013 Mayer et al.
8,361,157 B2 1/2013 Bouttens et al.
8,425,614 B2 4/2013 Winslow et al.
8,444,680 B2 5/2013 Dooney, Jr. et al.
8,449,617 B1 5/2013 McDaniel et al.
8,454,702 B2 6/2013 Smits et al.
8,454,705 B2 6/2013 Pressacco et al.
8,465,548 B2 6/2013 Long
8,480,750 B2 7/2013 Long
8,532,806 B1 9/2013 Masson
8,556,901 B2 10/2013 Anthony et al.
8,556,902 B2 10/2013 Ek et al.
8,556,980 B2 10/2013 Deffenbaugh
8,556,981 B2 10/2013 Jones et al.
8,591,591 B2 11/2013 Winslow et al.
8,597,334 B2 12/2013 Mocanu
8,632,597 B2 1/2014 Lappin
8,690,951 B2 4/2014 Baum et al.
8,690,952 B2 4/2014 Dallmann
8,753,402 B2 6/2014 Winslow et al.
8,790,402 B2 7/2014 Monaghan et al.
8,840,676 B2 9/2014 Belew et al.
8,864,834 B2 10/2014 Boileau et al.
8,870,886 B2 10/2014 Burgi
8,961,611 B2 2/2015 Long
9,114,017 B2 8/2015 Lappin
9,233,003 B2 1/2016 Roche et al.
9,498,345 B2 11/2016 Burkhead, Jr. et al.
9,629,725 B2 4/2017 Gargac et al.
9,763,682 B2 9/2017 Bettenga
9,782,208 B2 10/2017 Martin
9,839,436 B2 12/2017 Kehres et al.
10,034,757 B2 7/2018 Kovacs et al.
10,064,734 B2 9/2018 Burkhead, Jr. et al.
10,251,755 B2 4/2019 Boileau et al.
10,342,669 B2 7/2019 Hopkins
10,357,373 B2 7/2019 Gargac et al.
10,463,499 B2 11/2019 Emerick et al.
10,583,012 B1 3/2020 Longobardi
10,722,374 B2 7/2020 Hodorek et al.
10,918,492 B2 2/2021 Burkhead, Jr. et al.
10,945,862 B2 3/2021 Roby et al.
11,564,802 B2 * 1/2023 Ball ...................... A61F 2/4612
2001/0011192 A1 8/2001 Ondrla et al.
2001/0037153 A1 11/2001 Rockwood, Jr. et al.
2002/0095214 A1 7/2002 Hyde, Jr.
2003/0055507 A1 3/2003 McDevitt et al.
2003/0149485 A1 8/2003 Tornier
2004/0030394 A1 2/2004 Horber
2004/0059424 A1 3/2004 Guederian et al.
2004/0106928 A1 6/2004 Ek
2004/0220673 A1 11/2004 Pria
2004/0220674 A1 11/2004 Pria
2004/0225367 A1 11/2004 Glien et al.
2005/0049709 A1 3/2005 Tornier
2005/0060039 A1 3/2005 Cyprien
2005/0085915 A1 4/2005 Steinberg
2005/0143831 A1 6/2005 Justin et al.
2005/0149044 A1 7/2005 Justin et al.
2005/0192673 A1 9/2005 Saltzman et al.
2005/0256583 A1 11/2005 Bouttens et al.
2005/0261775 A1 11/2005 Baum et al.
2005/0278030 A1 12/2005 Tornier et al.
2006/0069443 A1 3/2006 Deffenbaugh et al.
2006/0069444 A1 3/2006 Deffenbaugh
2006/0074353 A1 4/2006 Deffenbaugh et al.
2006/0074430 A1 4/2006 Deffenbaugh et al.
2006/0100714 A1 5/2006 Ensign
2006/0111787 A1 5/2006 Bailie et al.
2006/0122705 A1 6/2006 Morgan
2006/0142865 A1 6/2006 Hyde, Jr.
2006/0200248 A1 9/2006 Beguin et al.
2006/0200249 A1 9/2006 Beguin et al.
2007/0016304 A1 1/2007 Chudik
2007/0055380 A1 3/2007 Berelsman et al.
2007/0100458 A1 5/2007 Dalla Pria

(56) References Cited

U.S. PATENT DOCUMENTS

2007/0142921 A1 6/2007 Lewis et al.
2007/0142922 A1 6/2007 Lewis et al.
2007/0156246 A1 7/2007 Meswania et al.
2007/0179624 A1 8/2007 Stone et al.
2007/0219638 A1 9/2007 Jones et al.
2007/0244563 A1 10/2007 Roche et al.
2007/0244564 A1 10/2007 Ferrand et al.
2007/0260321 A1 11/2007 Stchur
2008/0140130 A1 6/2008 Chan et al.
2008/0183297 A1 7/2008 Boileau et al.
2008/0255568 A1 10/2008 Tornier et al.
2008/0269906 A1 10/2008 Iannotti et al.
2008/0294268 A1 11/2008 Baum et al.
2008/0306601 A1 12/2008 Dreyfuss
2009/0125113 A1 5/2009 Guederian et al.
2009/0149961 A1 6/2009 Dallmann
2009/0164021 A1 6/2009 Dallmann
2009/0204225 A1 8/2009 Meridew et al.
2009/0216332 A1 8/2009 Splieth et al.
2009/0281630 A1 11/2009 Delince et al.
2009/0281632 A1 11/2009 Naidu
2009/0292364 A1 11/2009 Linares
2010/0016975 A1 1/2010 Iannotti et al.
2010/0023068 A1 1/2010 Bouttens et al.
2010/0049327 A1 2/2010 Isch et al.
2010/0087927 A1 4/2010 Roche et al.
2010/0161066 A1 6/2010 Iannotti et al.
2010/0217399 A1 8/2010 Groh
2010/0234959 A1 9/2010 Roche et al.
2010/0249938 A1 9/2010 Gunther et al.
2010/0274359 A1 10/2010 Brunnarius et al.
2010/0291401 A1 11/2010 Medina et al.
2010/0331990 A1 12/2010 Mroczkowski et al.
2011/0029089 A1 2/2011 Giuliani et al.
2011/0035013 A1 2/2011 Winslow et al.
2011/0106266 A1 5/2011 Schwyzer et al.
2011/0118846 A1 5/2011 Katrana et al.
2011/0137417 A1 6/2011 Lee
2011/0144758 A1 6/2011 Deffenbaugh
2011/0144760 A1 6/2011 Wong et al.
2011/0152869 A1 6/2011 Ek et al.
2011/0190899 A1 8/2011 Pierce et al.
2011/0224673 A1 9/2011 Smith
2011/0276144 A1 11/2011 Wirth et al.
2011/0282393 A1 11/2011 Gerlach et al.
2012/0004733 A1 1/2012 Hodorek et al.
2012/0029647 A1 2/2012 Winslow et al.
2012/0035734 A1 2/2012 Unwin et al.
2012/0078258 A1 3/2012 Lo et al.
2012/0109320 A1 5/2012 Walch et al.
2012/0123419 A1 5/2012 Purdy et al.
2012/0130498 A1 5/2012 Long
2012/0165954 A1 6/2012 Nimal
2012/0191201 A1 7/2012 Smits et al.
2012/0209392 A1 8/2012 Angibaud et al.
2012/0221111 A1 8/2012 Burkhead, Jr. et al.
2012/0221112 A1 8/2012 Lappin
2012/0232670 A1 9/2012 Bojarski et al.
2012/0239051 A1 9/2012 de Wilde et al.
2012/0239156 A1 9/2012 de Wilde et al.
2012/0253467 A1 10/2012 Frankle
2012/0277880 A1 11/2012 Winslow et al.
2013/0018483 A1 1/2013 Li et al.
2013/0053968 A1 2/2013 Nardini et al.
2013/0066433 A1 3/2013 Veronesi et al.
2013/0096631 A1 4/2013 Leung et al.
2013/0110116 A1 5/2013 Kehres et al.
2013/0110470 A1 5/2013 Vanasse et al.
2013/0144393 A1 6/2013 Mutchler et al.
2013/0150972 A1 6/2013 Iannotti et al.
2013/0150973 A1 6/2013 Splieth et al.
2013/0150975 A1 6/2013 Iannotti et al.
2013/0204375 A1 8/2013 Winslow et al.
2013/0226186 A1 8/2013 Burgi
2013/0226309 A1 8/2013 Daigo et al.
2013/0231754 A1 9/2013 Daigo et al.
2013/0253656 A1 9/2013 Long
2013/0261751 A1 10/2013 Lappin
2013/0261752 A1 10/2013 Lappin et al.
2013/0264749 A1 10/2013 Jones et al.
2013/0282135 A1 10/2013 Sun et al.
2013/0338675 A1 12/2013 Nelson et al.
2014/0005789 A1 1/2014 Chavarria et al.
2014/0012266 A1 1/2014 Bonin, Jr. et al.
2014/0018927 A1 1/2014 de Wilde et al.
2014/0025173 A1 1/2014 Cardon et al.
2014/0142711 A1 5/2014 Maroney et al.
2014/0163564 A1 6/2014 Bollinger
2014/0188231 A1 7/2014 Poncet et al.
2014/0194995 A1 7/2014 Koka
2014/0243986 A1 8/2014 Frankle
2014/0257499 A1 9/2014 Winslow et al.
2014/0277180 A1 9/2014 Paolino et al.
2014/0277517 A1 9/2014 Winslow
2014/0277518 A1 9/2014 Iannotti
2014/0277520 A1 9/2014 Chavarria et al.
2014/0316416 A1 10/2014 Liu et al.
2014/0371863 A1 12/2014 Vanasse et al.
2015/0059383 A1 3/2015 Sakamoto et al.
2015/0073424 A1 3/2015 Couture et al.
2015/0094819 A1 4/2015 Iannotti et al.
2015/0142122 A1 5/2015 Bickley et al.
2015/0150688 A1 6/2015 Vanasse et al.
2015/0265292 A1 9/2015 Olson
2015/0265411 A1 9/2015 Deransart et al.
2015/0272741 A1 10/2015 Taylor et al.
2015/0305877 A1 10/2015 Gargac et al.
2016/0045323 A1 2/2016 Kovacs et al.
2016/0151164 A1 6/2016 Taylor et al.
2016/0166392 A1 6/2016 Vanasse et al.
2016/0199074 A1 7/2016 Winslow et al.
2016/0206436 A1 7/2016 Chavarria et al.
2016/0228262 A1 8/2016 Bailey
2016/0256222 A1 9/2016 Walch
2016/0270922 A1 9/2016 Pressacco et al.
2016/0278794 A1 9/2016 Boldt et al.
2016/0287266 A1 10/2016 Sikora et al.
2016/0287401 A1 10/2016 Muir et al.
2016/0310285 A1 10/2016 Kovacs et al.
2016/0324649 A1 11/2016 Hodorek et al.
2016/0354209 A1 12/2016 Van Kampen et al.
2016/0367375 A1 12/2016 Boulris
2017/0027709 A1 2/2017 Winslow et al.
2017/0042687 A1 2/2017 Boileau et al.
2017/0042690 A1 2/2017 Burkhead, Jr. et al.
2017/0049574 A1 2/2017 Hopkins
2017/0172764 A1 6/2017 Muir et al.
2017/0273795 A1 9/2017 Neichel et al.
2017/0273801 A1 9/2017 Hodorek
2017/0273806 A1 9/2017 Cardon et al.
2017/0319348 A1 11/2017 Goldberg
2017/0367836 A1 12/2017 Cardon et al.
2018/0014941 A1 1/2018 Frankle et al.
2018/0064537 A1 3/2018 Pressacco et al.
2018/0078377 A1 3/2018 Gargac et al.
2018/0085226 A1 3/2018 Baumgarten
2018/0092747 A1 4/2018 Hopkins
2018/0161169 A1 6/2018 Cardon et al.
2018/0243102 A1 8/2018 Burkhead, Jr. et al.
2018/0303618 A1 10/2018 Kovacs et al.
2018/0368982 A1 12/2018 Ball
2019/0015116 A1 1/2019 Gargac et al.
2019/0015117 A1 1/2019 Neichel et al.
2019/0015221 A1 1/2019 Neichel et al.
2019/0029833 A1 1/2019 Briscoe et al.
2019/0076261 A1 3/2019 Mutchler et al.
2019/0336293 A1 11/2019 Kehres
2020/0030108 A1 1/2020 Orphanos et al.
2020/0179126 A1 6/2020 Courtney, Jr. et al.
2020/0188125 A1 6/2020 Hodorek et al.
2020/0237519 A1 7/2020 Ball et al.
2020/0289180 A1 9/2020 Martin et al.
2020/0289282 A1 9/2020 Lefebvre et al.
2020/0368031 A1 11/2020 Hodorek et al.

(56) References Cited

U.S. PATENT DOCUMENTS

| | | | |
|---|---|---|---|
| 2020/0405491 | A1 | 12/2020 | Cleveland et al. |
| 2021/0030552 | A1 | 2/2021 | Terrill |
| 2021/0030553 | A1 | 2/2021 | Terrill |
| 2021/0045895 | A1 | 2/2021 | Sapio et al. |
| 2021/0298910 | A1 | 9/2021 | Gargac et al. |
| 2021/0307911 | A1 | 10/2021 | Metcalfe et al. |
| 2021/0307919 | A1 | 10/2021 | Paterson et al. |
| 2021/0338456 | A1 | 11/2021 | Wolfe et al. |
| 2021/0369465 | A1 | 12/2021 | Simoes et al. |
| 2022/0110757 | A1 | 4/2022 | Paterson |
| 2022/0142789 | A1 | 5/2022 | Axelson, Jr. et al. |
| 2022/0151793 | A1 | 5/2022 | Deransart et al. |
| 2022/0151794 | A1 | 5/2022 | Fattori et al. |
| 2022/0151795 | A1 | 5/2022 | Running et al. |
| 2022/0175543 | A1 | 6/2022 | Ball |
| 2022/0183851 | A1 | 6/2022 | Deransart et al. |
| 2022/0202580 | A1 | 6/2022 | Wilkins et al. |
| 2022/0202583 | A1 | 6/2022 | Axelson, Jr. et al. |
| 2022/0241077 | A1 | 8/2022 | Hodorek et al. |
| 2022/0280306 | A1 | 9/2022 | Metcalfe et al. |
| 2022/0296381 | A1 | 9/2022 | Ek et al. |
| 2022/0313440 | A1 | 10/2022 | Metcalfe et al. |
| 2022/0395376 | A1 | 12/2022 | Poon et al. |
| 2023/0000636 | A1 | 1/2023 | Dalla Pria et al. |
| 2023/0114073 | A1 | 4/2023 | Perego |
| 2023/0285154 | A1 | 9/2023 | Picha et al. |

FOREIGN PATENT DOCUMENTS

| | | | |
|---|---|---|---|
| DE | 10123517 | C1 | 11/2002 |
| EP | 0581667 | A1 | 2/1994 |
| EP | 0776636 | A1 | 6/1997 |
| EP | 1013246 | A1 | 6/2000 |
| EP | 1064890 | A1 | 1/2001 |
| EP | 1323395 | A1 | 7/2003 |
| EP | 1488764 | B1 | 12/2006 |
| EP | 1762201 | A1 | 3/2007 |
| EP | 1639949 | B1 | 8/2007 |
| EP | 1639967 | B1 | 7/2008 |
| EP | 1515758 | B1 | 3/2009 |
| EP | 1776935 | B1 | 8/2009 |
| EP | 1639966 | A1 | 9/2009 |
| EP | 2201912 | A1 | 6/2010 |
| EP | 1927328 | B1 | 1/2011 |
| EP | 1902689 | B1 | 11/2011 |
| EP | 2564814 | A1 | 3/2013 |
| EP | 1996125 | B1 | 5/2013 |
| EP | 2335655 | B1 | 7/2013 |
| EP | 1951161 | B1 | 4/2014 |
| EP | 1973498 | B1 | 4/2014 |
| EP | 2481376 | B1 | 4/2014 |
| EP | 2057970 | B1 | 1/2016 |
| EP | 2601912 | B1 | 7/2016 |
| EP | 3291768 | A1 | 3/2018 |
| EP | 3412252 | B1 | 2/2020 |
| EP | 3679900 | A1 | 7/2020 |
| EP | 3756625 | A1 | 12/2020 |
| FR | 2567019 | A1 | 1/1986 |
| FR | 2739151 | A1 | 3/1997 |
| FR | 2776506 | B1 | 8/2000 |
| FR | 2790662 | B1 | 6/2001 |
| FR | 2825263 | A1 | 12/2002 |
| FR | 2821545 | B1 | 8/2003 |
| FR | 2955248 | B1 | 3/2012 |
| FR | 2971144 | A1 | 8/2012 |
| FR | 2977791 | B1 | 7/2014 |
| GB | 2297257 | A | 7/1996 |
| JP | 2015516835 | A | 6/2015 |
| JP | 2015532863 | A | 11/2015 |
| JP | 2016187553 | A | 11/2016 |
| WO | 2001054561 | A2 | 8/2001 |
| WO | 2010076534 | A1 | 7/2010 |
| WO | 2011044879 | A1 | 4/2011 |
| WO | 2011073169 | A1 | 6/2011 |
| WO | 2011150180 | A2 | 12/2011 |
| WO | 2013064569 | A1 | 5/2013 |
| WO | 2015051476 | A1 | 4/2015 |
| WO | 2015068035 | A1 | 5/2015 |
| WO | 2015103090 | A1 | 7/2015 |
| WO | 2015130006 | A1 | 9/2015 |
| WO | 2016025712 | A2 | 2/2016 |
| WO | 2017007565 | A2 | 1/2017 |
| WO | 2019014278 | A1 | 1/2019 |
| WO | 2019079104 | A2 | 4/2019 |
| WO | 2020033911 | A1 | 2/2020 |
| WO | 2020154611 | A1 | 7/2020 |
| WO | 2020219962 | A1 | 10/2020 |
| WO | 2020231657 | A1 | 11/2020 |
| WO | 2021030146 | A1 | 2/2021 |
| WO | 2021178418 | A1 | 9/2021 |
| WO | 2021216405 | A3 | 12/2021 |
| WO | 2022147376 | A1 | 7/2022 |
| WO | 2022261508 | A1 | 12/2022 |
| WO | 2023018485 | A1 | 2/2023 |
| WO | 2024015899 | A2 | 1/2024 |

OTHER PUBLICATIONS

Extended European Search Report issued in connection with European Patent Application No. 22856384.7, Mar. 18, 2025, 5 pages.

Extended European Search Report issued in connection with European Patent Application No. 24219566.7, Mar. 27, 2025, 8 pages.

International Search Report and Written Opinion issued in connection with International Patent Application No. PCT/US2025/016710, Apr. 8, 2025, 11 pages.

International Search Report and Written Opinion issued in connection with International Patent Application No. PCT/US2022/080550, Apr. 10, 2023, 16 pages.

EP Search Report and Written Opinion issued in European Patent Application No. 12153346.7, dated Mar. 8, 2012, in 6 pages.

French Search Report and Written Opinion issued in Application. No. FR1150994, mailed May 27, 2011, in 7 pages.

Anatomical ShoulderTM Inverse/Reverse System Surgical Technique, Product Brochure, Zimmer, Inc., published 2006, in 32 pages.

Arthrex, "Arthrex Releases Univers ReversTM Shoulder Arthroplasty System in the United States—First Surgery Successfully Performed in Chillicothe, OH", Jun. 18, 2013.

Biomet, "Comprehensive ® Reverse Shoulder System", 2013.

Boileau et al., "Cemented polyethylene versus uncemented metal-backed glenoid components in total shoulder arthroplasty: A prospective, double-blind, randomized study," Journal of Shoulder and Elbow Surgery, Jul./Aug. 2002, vol. 11, Issue 4, pp. 351-359.

Boileau et al., "Metal-backed glenoid implant with polyethylene insert is not a viable long-term therapeutic option," Journal of Shoulder and Elbow Surgery, Feb. 2015, pp. 1-10.

Cementless Fixation Using a Polyethyene Oseo-Integration Peg as Used on the Freeman-Samuelson Knee brochure, produced by Finsbury Instruments Limited London in conjunction with Adrian Tuke Limited, 1982.

Castagna et al., "Mid-term results of a metal-backed glenoid component in total shoulder replacement," The Journal of Bone and Joint Surgery, Oct. 2010, vol. 92-B, No. 10, pp. 1410-1415.

Clement et al., "An uncemented metal-backed glenoid component in total shoulder arthroplasty for osteoarthritis: factors affecting survival and outcome," The Japanese Orthopaedic Association, published online Sep. 26, 2012, vol. 18, pp. 22-28.

DJO Surgical, Reverse® shoulder prosthesis Surgical Technique, Feb. 2008.

EclipseTM Stemless Shoulder Prosthesis, Surgical Technique Guide, Anthrex GmbH, 2014, in 12 pages.

Epoca Shoulder Arthroplasty System, Synthes, Inc., Apr. 2008, in 4 pages.

Epoca Shoulder Arthroplasty System—Stem and Glenoid Technique Guide, Synthes, Inc., Apr. 2008, in 56 pages.

Innovative Design Orthopaedics, "Verso® Shoulder Surgical Technique", 2013.

(56) References Cited

OTHER PUBLICATIONS

Kany et al., "A convertible shoulder system: is it useful in total shoulder arthroplasty revisions?" International Orthopaedics, published online Oct. 16, 2014, vol. 39, pp. 299-304.
Katz et al., "New design of a cementless glenoid component in unconstrained shoulder arthroplasty: a prospective medium-term analysis of 143 cases," published online Oct. 27, 2012, vol. 23, pp. 27-34.
Montoya et al., "Midterm results of a total shoulder prosthesis fixed with a cementless glenoid component," Journal of Shoulder and Elbow Surgery, May 2013, vol. 22, Issue 5, pp. 628-635.
SMR Axioma® TT Metal Back Surgical Technique, Product Brochure, Lima Corporate, dated Sep. 2013, in 48 pages.
Taunton et al., "Total Shoulder Arthroplasty with a Metal-Backed, Bone-Ingrowth Glenoid Component," The Journal of Bone and Joint Surgery, Oct. 2008, vol. 90-A, Issue 10, pp. 2180-2188.
Teissier et al., "The TESS reverse shoulder arthroplasty without a stem in the treatment of cuff-deficient shoulder conditions: clinical and radiographic results," Journal of Shoulder and Elbow Surgery, Jan. 2015, vol. 24, Issue 1, pp. 45-51.
The Anatomical ShoulderTM: A true system approach, Product Brochure, Zimmer UK Ltd, printed 2006, in 6 pages.
Univers ReversTM Total Shoulder System, Surgical Technique Guide, Anthrex Inc., Version D, revised Jul. 2, 2015, in 28 pages.
International Search Report and Written Opinion issued in connection with International Patent Application No. PCT/US2022/034245, Sep. 23, 2022, 16 pages.
Non-Final Office Action issued in connection with U.S. Appl. No. 16/756,429, filed May 6, 2022, 24 pages.
International Search Report and Written Opinion issued in connection with International Patent Application No. PCT/US2022/011217, May 4, 2022, 15 pages.
International Search Report and Written Opinion issued in connection with International Patent Application No. PCT/US2022/016106, May 11, 2022, 12 pages.
International Search Report and Written Opinion issued in connection with International Patent Application No. PCT/US2020/045211 dated Dec. 17, 2020, 19 pages.
International Search Report and Written Opinion for PCT International Application No. PCT/US2020/031134 issued Sep. 30, 2020.
International Search Report and Written Opinion for PCT International Application No. PCT/US2020/035217, Nov. 1, 2022, 14 pages.
Extended European Search Report issued in connection with European Patent Application No. 22760169.7, Oct. 29, 2024, 9 pages.
Partial European Search Report issued in connection with European Patent Application No. 24191670.9, Oct. 18, 2024, 11 pages.
Second Examination Report issued in connection with Australian Patent Application No. 2022227496, Aug. 29, 2024, 7 pages.
Non-Final Office Action issued in connection with U.S. Appl. No. 18/539,598, filed Sep. 17, 2024, 9 pages.
Non-Final Office Action issued in connection with U.S. Appl. No. 17/149,308, filed May 23, 2023, 12 pages.
First Examination Report issued in connection with Australian Patent Application No. 2022227496, May 16, 2024, 5 pages.
Extended European Search Report issued in connection with European Patent Application No. 22201630.5, Feb. 9, 2023, 8 pages.
International Search Report and Written Opinion issued in connection with International Patent Application No. PCT/US2023/064983, Sep. 29, 2023, 10 pages.
International Search Report and Written Opinion issued in connection with International Patent Application No. PCT/US2023/070118, Mar. 1, 2024, 15 pages.
Extended European Search Report issued in connection with European Patent Application No. 21916574.3, Jul. 4, 2024, 8 pages.
Extended European Search Report issued in connection with European Patent Application No. 22753403.9, Jul. 4, 2024, 8 pages.
Extended European Search Report issued in connection with European Patent Application No. 24191670.9, Feb. 20, 2025, 13 pages.
Communication Under Rule 164(2)(b) issued in connection with European Patent Application No. 20758408.7, Feb. 28, 2025, 9 pages.
International Search Report and Written Opinion issued in connection with International Patent Application No. PCT/US2024/050431, Feb. 11, 2025, 7 pages.
First Office Action issued in connection with Japanese Patent Application No. 2023-532755, Jul. 9, 2024, 4 pages.
Examination Report issued in connection with Australian Patent Application No. 202143348, Jun. 28, 2024, 6 pages.
Non-Final Office Action issued in connection with U.S. Appl. No. 17/597,486, filed Jul. 16, 2024, 8 pages.
Second Office Action issued in connection with Japanese Patent Application No. 2022-507908, Jun. 20, 2023, 7 pages.
Notice of Allowance issued in connection with U.S. Appl. No. 17/172,789, filed Jul. 20, 2023, 8 pages.
Notice of Grant issued in connection with Japanese Patent Application No. 2023-547279, Dec. 10, 2024, 3 pages.
Advisory Action issued in connection with U.S. Appl. No. 17/432,228, filed Dec. 31, 2024, 3 pages.
Extended European Search Report issued in connection with European Patent Application No. 25192102.9, Nov. 12, 2025, 7 pages.
First Office Action issued in connection with Japanese Patent Application No. 2025-501428, Dec. 16, 2025, 6 pages.
Examination Report issued in connection with European Patent Application No. 21916574.3, Dec. 2, 2025, 6 pages.
Non-Final Office Action issued in connection with U.S. Appl. No. 18/046,297, filed Sep. 17, 2025, 18 pages.
Extended European Search Report issued in connection with European Patent Application No. 22899583.3, Oct. 16, 2025, 15 pages.
Extended European Search Report issued in connection with European Patent Application No. 23840520.3, Feb. 24, 2026, 7 pages.
First Office Action issued in Chinese Patent Application No. 202180088483.3, Apr. 21, 2026, 6 pages.

* cited by examiner 212
216
210
214
218
220
282
286
280
284
290
272
274
260
270
278
262
264
240
234
266
232
238
236
250
200
230
252

SHOULDER IMPLANTS AND METHODS OF USE AND ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present disclosure relates generally to general surgery and orthopedic implants for replacing an articulation surface in a joint. More specifically, but not exclusively, the present invention relates to implants and methods for shoulder replacement surgery, including reverse shoulder replacement prostheses with offset components and coupling mechanisms.

Description of the Related Art

Traditional total shoulder joint replacement involves a humeral implant and glenoid implant. The humeral implant generally includes a metal sphere to replace the head of the humerus and the glenoid implant generally includes a glenoid socket for receiving the sphere attached to a portion of the scapula. However, where the soft tissue has been severely damaged, a reverse shoulder replacement may be used. A reverse shoulder replacement involves reversing the original sphere and glenoid by attaching the glenoid implant to the proximal aspect of the humerus and the convex sphere being attached to the glenoid fossa.

However, currently available replacement prostheses include a sphere and a baseplate that are generally centrally aligned and that utilize locking components to couple the sphere and baseplate together. These are hard to manufacture due to the taper, and can be poorly aligned resulting in limited articulation (e.g., range of motion) of the sphere. Also due to the alignment, disassembly of the sphere component can be challenging, often requiring an extractor claw or like tool which can cause tissue and bone damage that may create complications with the fixation of the baseplate.

Therefore, reverse shoulder prostheses that allows for a greater range of articulation, which are easier to manufacture, and which can be more readily disassembled are needed.

SUMMARY OF THE INVENTION

Aspects of the present disclosure provide implants and methods for replacing a shoulder joint. More specifically, the present disclosure provides humeral replacement prostheses and implants that include an offset post and a locking screw. By offsetting the post and other features, a more versatile prosthesis can be developed allowing for large offsets and differing shoulder sizes to be replaced. Further, the offset allows for easier access to the locking screw in order to disassemble the prosthesis with an extraction device. In this way, lower manufacturing costs are achieved on prostheses which are more adaptable and easier to disassemble.

In one aspect, provided herein is an implant. The implant, including a base member, an articulating member, and a coupling portion for securing the base member to the articulating member.

In another aspect, provided herein is a method of assembling an implant. The method of assembly includes obtaining a base member and inserting a first end of an elastic member into a projection of the base member. The method also includes engaging a first end of a first fixation component with a second end of the elastic member and sliding a second fixation component over a second end of the first fixation component and coupling the second fixation component to the projection. Further, the method includes coupling an articulating member with the first second end of the first fixation component.

In yet another aspect, provided herein is a method of using an implant. The method includes positioning a base member of the implant within a scapula and attaching an articulating member of the implant to the base member with a coupling portion positioned at least partially within a projection of the base member and the projection and a portion of the coupling portion extending into a cavity within the articulating member to engage a threaded portion in the cavity of the articulating member.

In still another aspect, provided herein is an extraction device for use with humeral prostheses. The extraction device engages a screw via a through hole in a sphere of the humeral prosthesis for disassembly of the sphere from a baseplate of the prosthesis.

In a further aspect, provided herein is a method for using a humeral prosthesis.

These, and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the humeral prostheses and related methods described herein, there is shown herein illustrative embodiments. These illustrative embodiments are in no way limiting in terms of the precise arrangement and operation of the disclosed humeral replacement prostheses and related methods and other similar embodiments are envisioned within the spirit and scope of the present disclosure. The accompanying drawings, which are incorporated in and constitute a part of the specification, illustrate embodiments of the disclosure and together with the detailed description herein, serve to explain the principles of the disclosure. The drawings are only for purposes of illustrating preferred embodiments and are not to be construed as limiting the disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION OF THE PREFERRED EMBODIMENT

Figure 1:
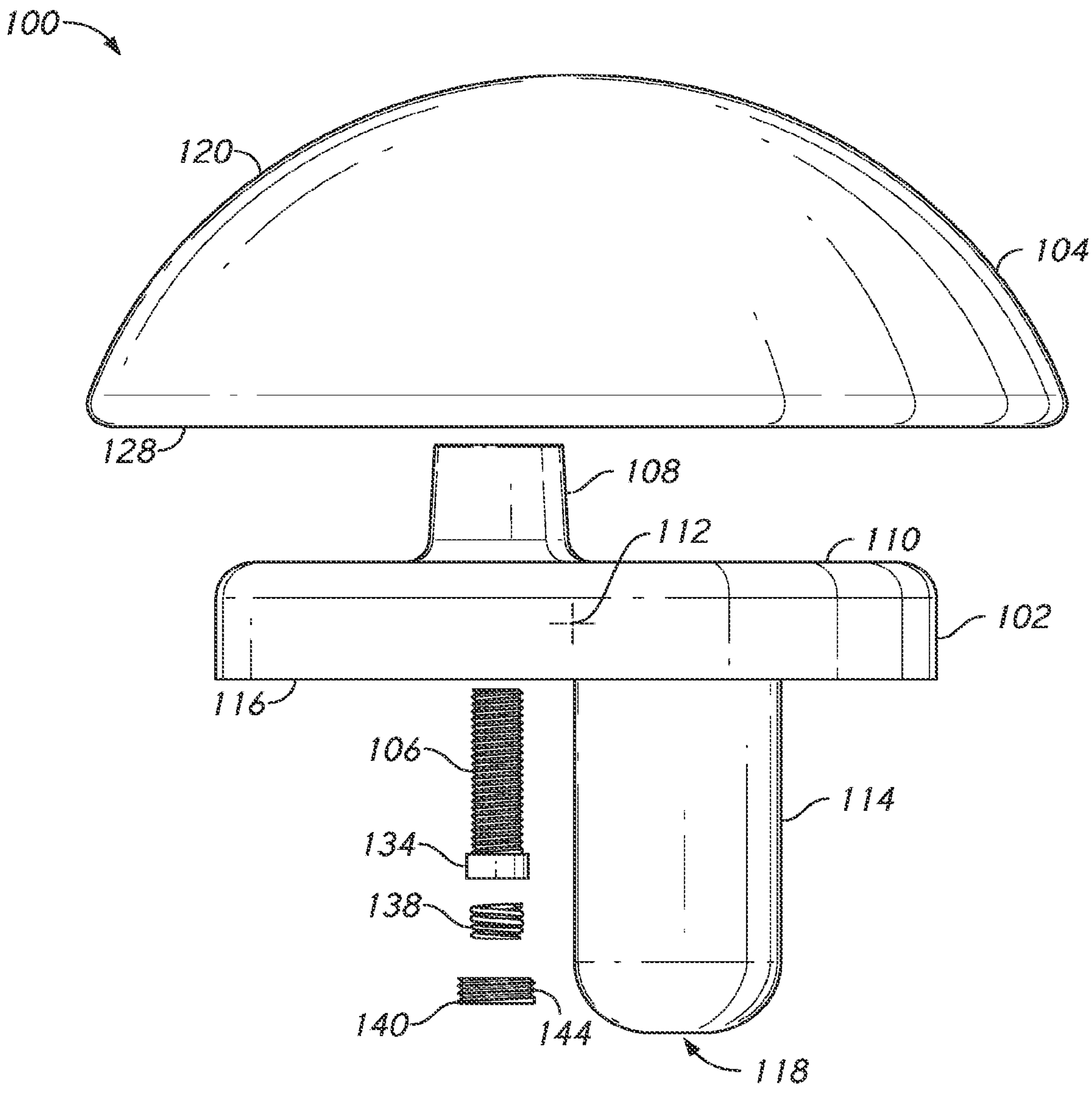
FIG. 1 is an exploded side view of an implant, in accordance with an aspect of the present disclosure.
Figure 2:
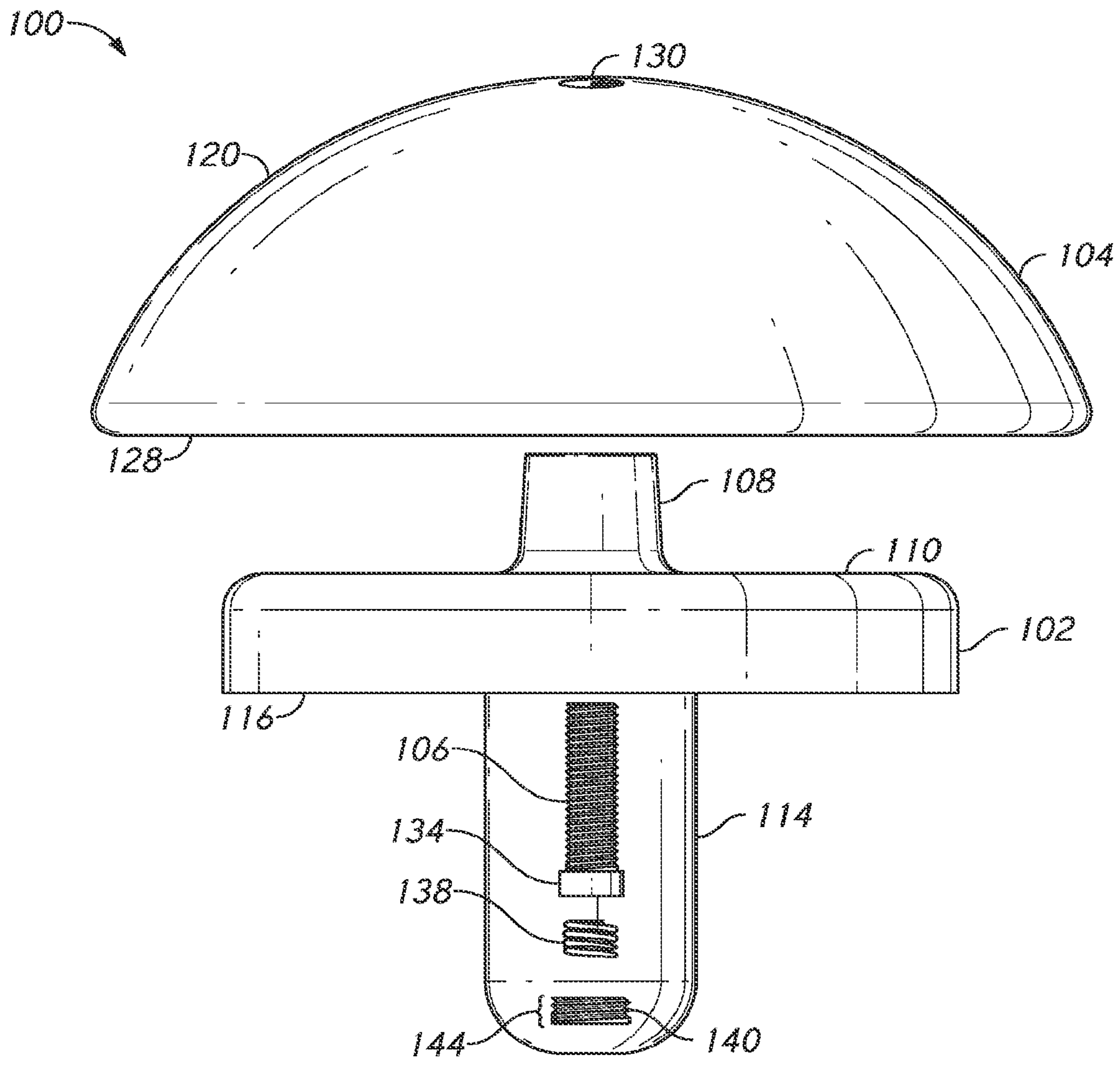
FIG. 2 is an exploded alternative side view of the implant of FIG. 1, in accordance with an aspect of the present disclosure.

Generally stated, disclosed herein are implants for replacing an articulation surface in a joint, for example, a shoulder. Further, surgical methods for replacing an articulation surface in the shoulder using the implants are discussed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current implants, devices, instrumentation and methods are described herein with reference to use with the bones of the shoulder, the bones of the shoulder, upper arm, and torso may be used to describe the surfaces, positions, directions or orientations of the implants, devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right shoulder may be mirrored so that they likewise function with the left shoulder. Further, the devices and methods, and the aspects, components, features and the like thereof, disclosed herein are described with respect to the shoulder for brevity purposes, but it should be understood that the devices and methods may be used with other bones of the body having similar structures, for example the upper extremity, and more specifically, with the bones of the shoulder, upper arm, and torso.

Referring to the drawings, wherein like reference numerals are used to indicate like or analogous components throughout the several views, and with particular reference to FIGS. 1-8, there are illustrated embodiments of a prosthesis or implant 100, for example, a humeral prosthesis or humeral implant. The terms "humeral implant" and "humeral prosthesis," as used herein, shall not be interpreted as limited to use in the humerus, but may also be used for implanting into the glenoid fossa to be utilized in a reverse shoulder configuration, as well as used in other like joints, as would be known by one of ordinary skill in the art. Methods for implanting and removing the implant 100, as well as a related extraction device are also disclosed. The prosthesis 100 may include a baseplate 102 (see FIGS. 1-8) for connection to a bone, an articulating component 104 (see FIGS. 1-8) for attaching to the baseplate 102, and a fixation component 106 (see FIGS. 1-6) for engaging a through hole 130 (see FIGS. 2 and 4) in the articulating component 104 to couple the baseplate 102 and the articulating component 104.

As shown in FIGS. 1-8, the baseplate 102 may include a projection 108 (see FIGS. 1-4 and 6) extending from a first side 110 (see FIGS. 1, 2, 4, and 6) of the baseplate 102. The projection 108 may be, for example, a Morse taper. The projection 108 may have a taper, for example, ranging between approximately 1° to 8°, as the projection 108 extends away from the baseplate 102. The projection 108 may be offset from a diametric center 112 (see FIG. 1) of the baseplate 102. The projection 108 may have, for example, a height and a diameter and the height may be larger than the diameter. The baseplate 102 may also include a post or stem 114 (see FIGS. 1-8) on a second side 116 (see FIGS. 1-3 and 5-8). The post 114 may also be offset relative to the center 112 of the baseplate 102, for example, diametrically offset from the projection 108. The post 114 may extend away from the second side 116 of the baseplate 102 to an end 118 of the post 114. The post 114 may be used to attach the baseplate 102 to the bone or to stabilize the baseplate 102 within a scapula or humerus. The post 114 may be of any length or cross sectional geometry necessary to be received within a bone and may be secured within the bone by any means, including but not limited to a surface treatment or structural elements, including ridges, fins, etc.

Figure 4:
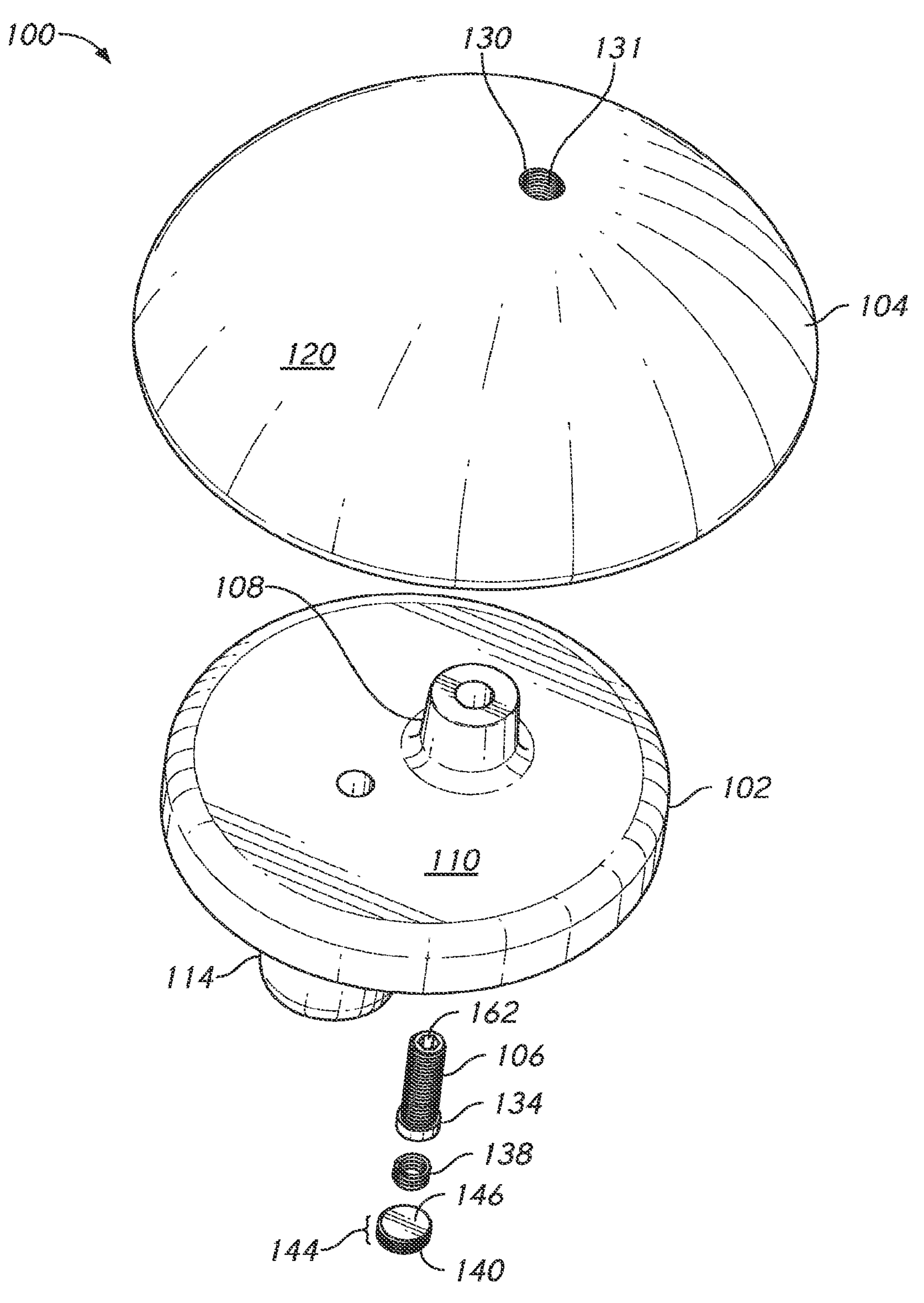
FIG. 4 is an exploded top perspective view of the implant of FIG. 1, in accordance with an aspect of the present disclosure.
Figure 5:
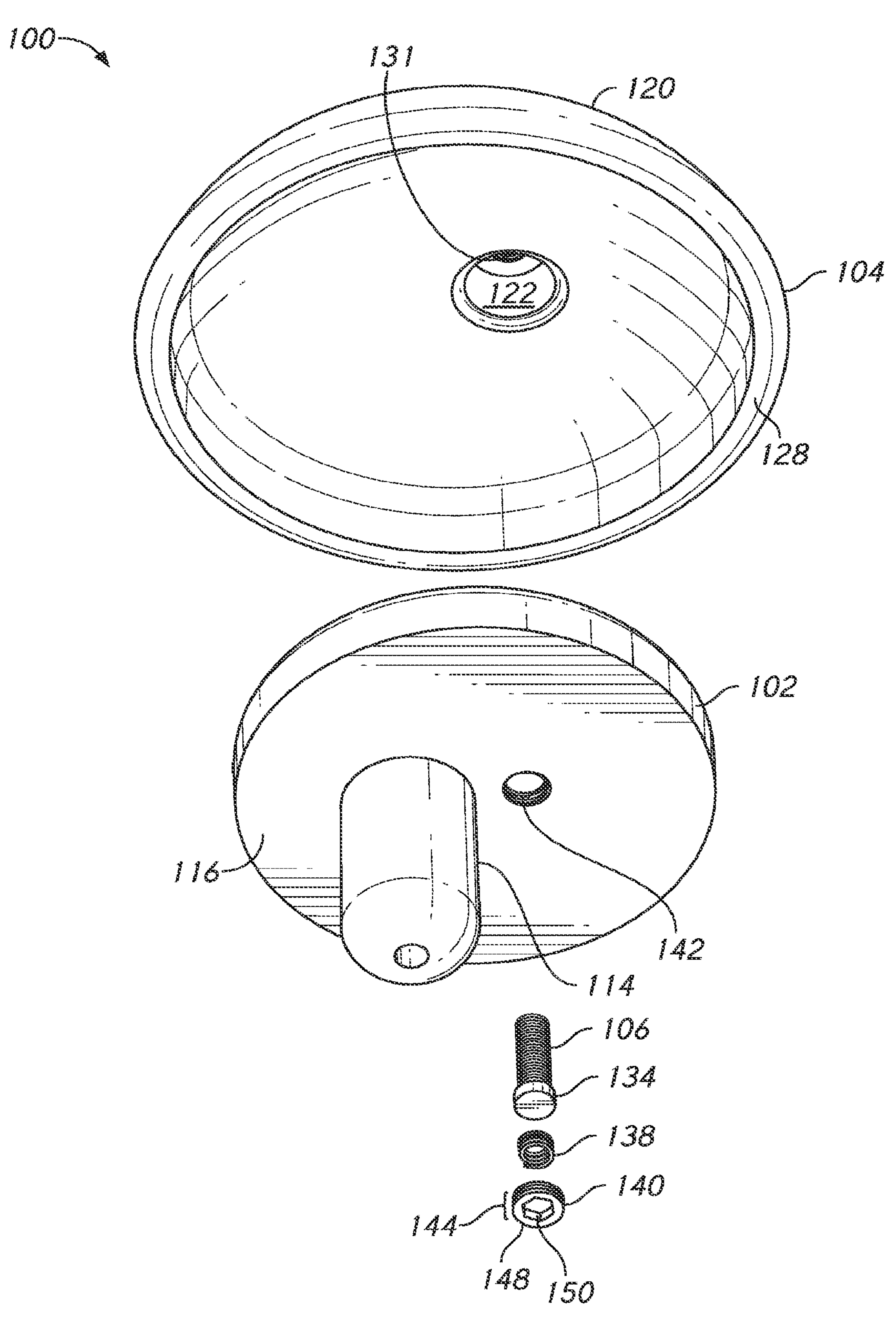
FIG. 5 is an exploded bottom perspective view of the implant of FIG. 1, in accordance with an aspect of the present disclosure.
Figure 6:
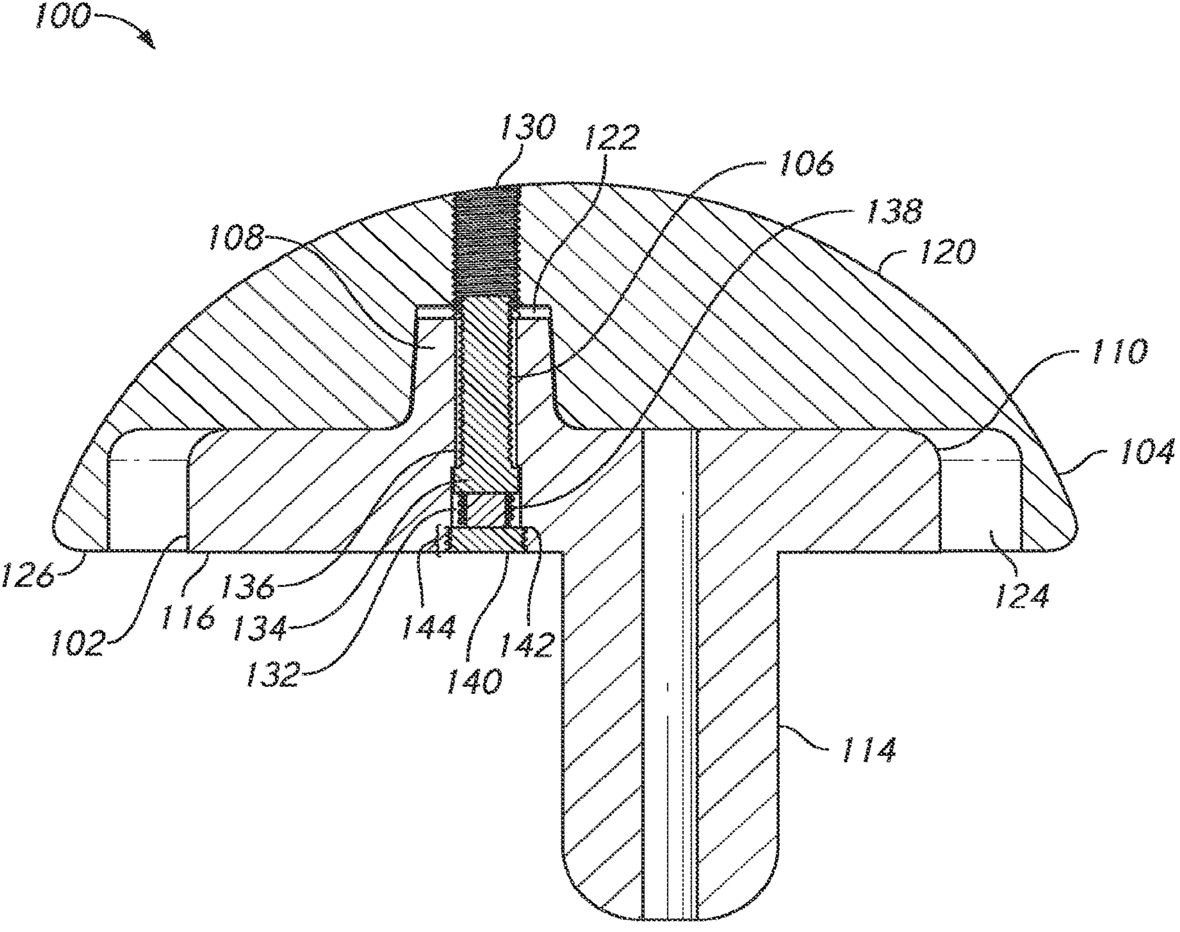
FIG. 6 is a semi-transparent, assembled side view of the implant of FIG. 1, in accordance with an aspect of the present disclosure.

As shown in FIGS. 1-6 and 8, the articulating component 104 may be, for example, a spherical shaped articulating component 104. The articulating component 104 attaches to the baseplate 102, can include, for example, a substantially convex side or articulating surface 120. As illustrated in FIG. 6, a cutaway view shows that the articulating component 104 may include a corresponding opening or cavity 122 for engaging or receiving the projection 108 of the baseplate 102. The opening 122 may be, for example, a corresponding Morse taper. The opening 122 (see FIGS. 3, 5, and 6) may be offset from a diametric center of the articulating component 104. As illustrated in FIG. 6, the articulating component 104 may include a recess 124 on the opposing side of the convex side 120 for accepting a top portion of the baseplate 102. The recess 124 may, for example, provide clearance around the baseplate 102 for inserting screws (not shown). In addition, the recess 124 allows for the base plate 102 to be inset into the articulating component 104 to position the engagement of the base plate 102 and articulating component 104 adjacent to the patient's bone. The articulating component 104 may also include a lip 126 about the diameter of the flat side 128 of the articulating component 104. The flat side 128 opposes the convex side 120. When assembled, the lip 126 will be substantially flush with the second side 116 of base plate 102 keeping the base plate 102 securely nested within the recess 124, as illustrated in FIG. 6. The cavity or Morse taper 122, is contained within the recess 124. The convex side 120 functions as the articulating surface would in a normal shoulder. The articulating component 104 can include a through hole 130 (see FIGS. 2, 4, and 6) extending from a first side, for instance the flat side 128, to a second side, for instance the convex side 120, of the articulating component 104. The through hole 130 may be threaded with a set of threads 131 as seen in the cutaway of FIG. 6, as well as in FIGS. 2, 4, and 5. In some embodiments, the through hole 130 is aligned with the cavity 122 as illustrated in FIG. 6.

Figure 3:
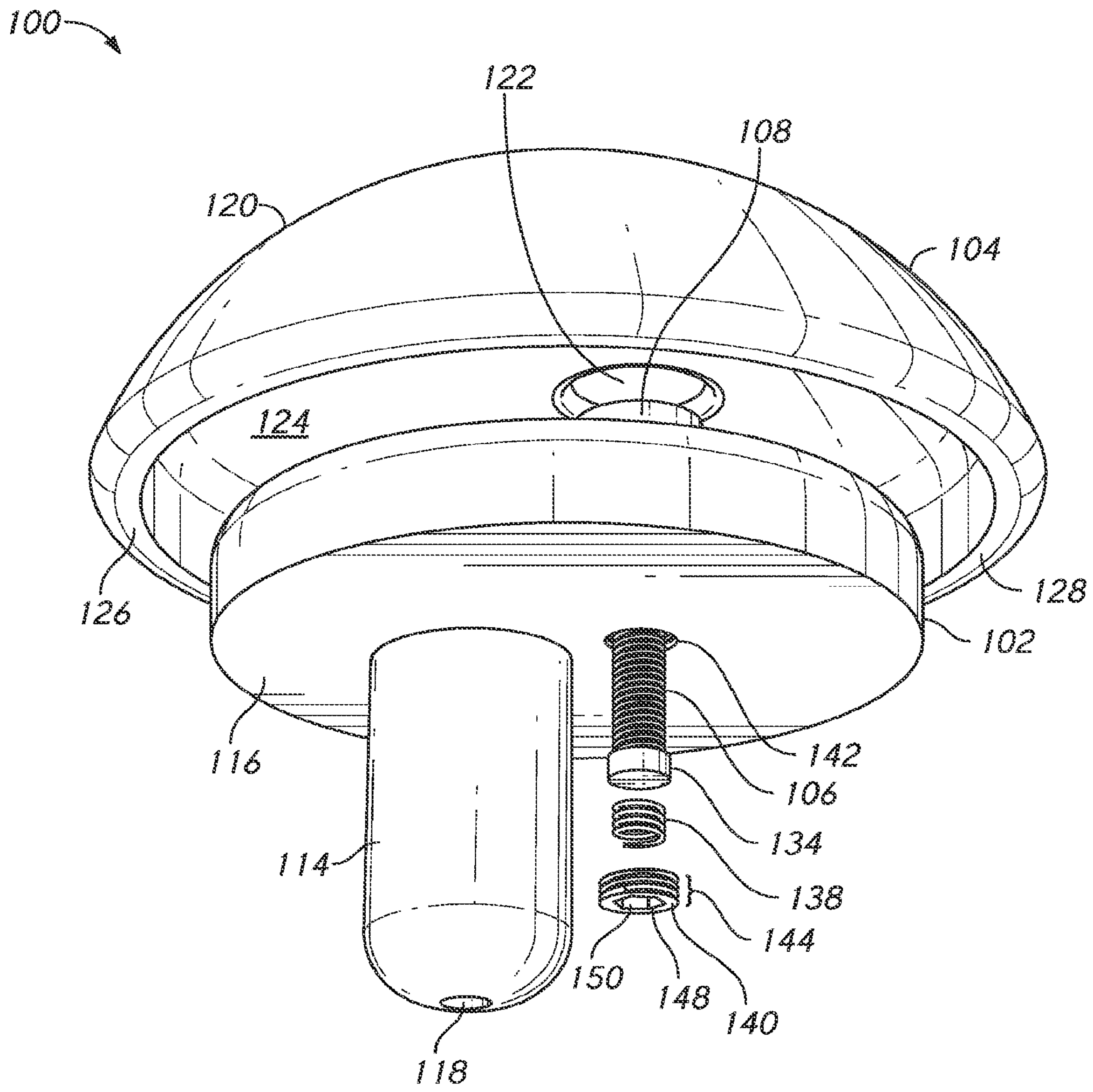
FIG. 3 is an exploded bottom perspective view of the implant of FIG. 1, in accordance with an aspect of the present disclosure.
Figure 7:
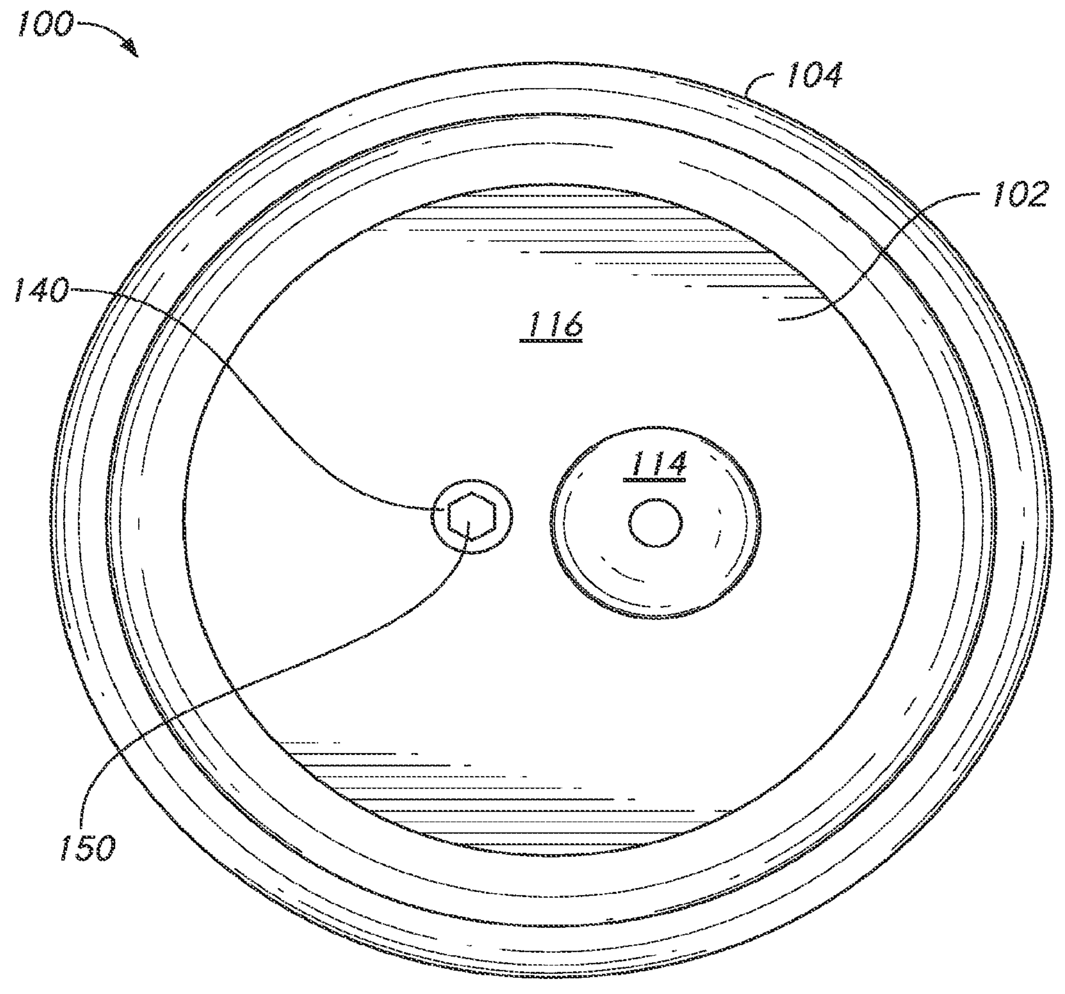
FIG. 7 is an assembled, bottom view of the implant of FIG. 1, in accordance with an aspect of the present disclosure.
Figure 8:
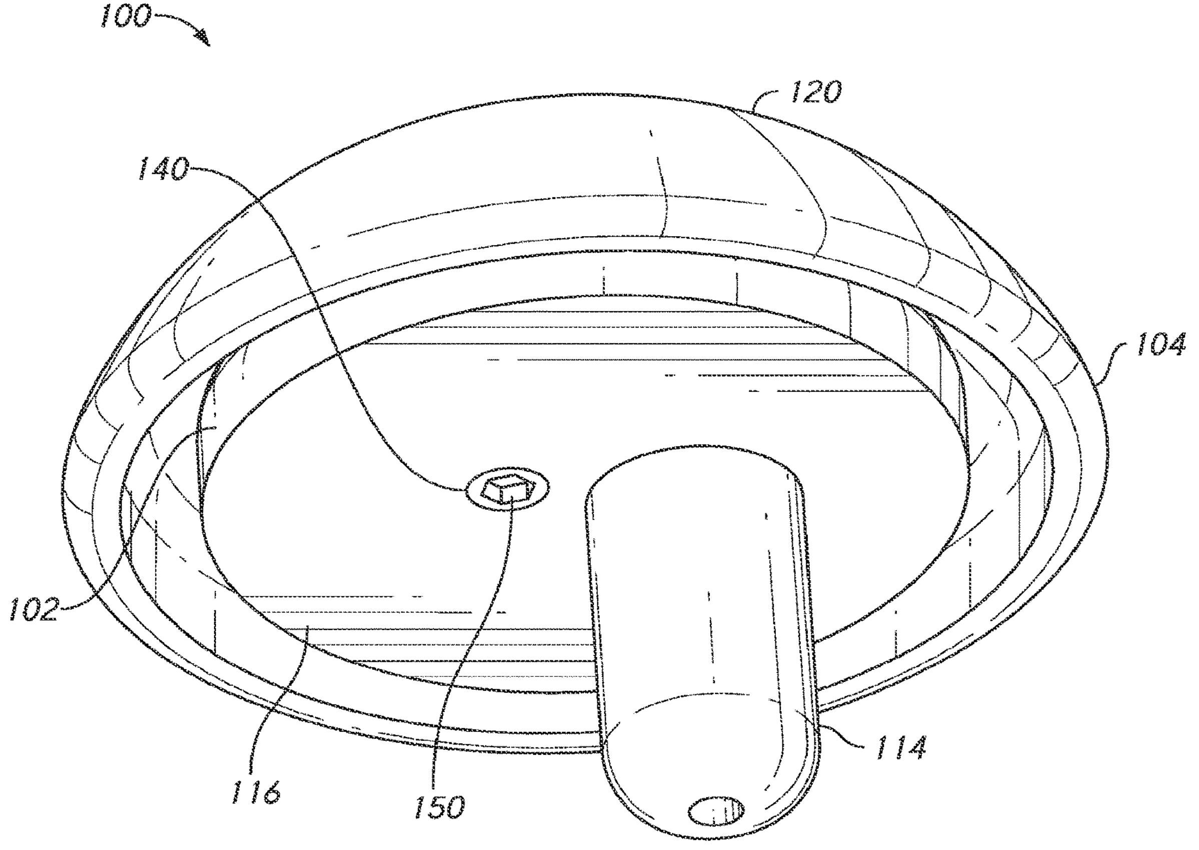
FIG. 8 is an assembled, bottom perspective view of the implant of FIG. 1, in accordance with an aspect of the present disclosure.

As shown in FIGS. 1-6, the fixation component 106 may engage or be configured to engage the through hole 130 in the articulating component 104. The fixation component 106 may also connect the baseplate 102 and the articulating component 104. The fixation component 106 may include, for example, any screw or like structure. The fixation component 106 may be contained within a cavity 132 of the baseplate 102. In some embodiments, the cavity 132 of the baseplate 102 is aligned with and contained partially within the projection 108 of the baseplate 102. As illustrated in FIGS. 1-6, the fixation component 106 may include a widened head 134, which may engage a lip 136 within the cavity 132. The widened head 134 may prevent the fixation component 106 from exiting the first side 110 of the baseplate 102. With continued reference to FIGS. 1-6, a spring 138 may be positioned between the head 134 of the fixation component 106 and a cap 140. This arrangement creates a biasing force to push the fixation component 106 out to engage the articulating component 104 when installed. Accordingly, the head 134 of the fixation component 106 may have a flat surface as illustrated in FIGS. 3 and 5. As noted above, the cap 140 may be positioned behind the fixation component 106 and the spring 138. The cap 140 may engage a threaded portion 142 of the cavity 132 to capture the spring 138 and the fixation component 106, which when assembled may fit flush on the second side 116 of the baseplate 102, as illustrated in FIGS. 6-8. In some embodiments, the cap 140, spring 138, and fixation component 106 may be preassembled before purchase of the prosthesis 100, limiting the number of parts needing to be assembled in the operating room.

As illustrated in FIGS. 1-6, the circumference 144 of cap 140 may be threaded in order to engage the threaded portion 142 of baseplate 102. As shown in FIG. 4, the internal surface 146 of cap 140 may be flat where the cap 140 will contact the spring 138. As shown in FIGS. 3, 5, 7, and 8, the external surface 148 of cap 140 may include an engagement surface 150, which may have, for example, any surface, shape, or feature for coupling or securing the cap 140 to the threaded portion 142 of baseplate 102.

Figure 9:
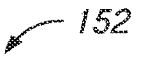
FIG. 9 is a side view of an extraction device, in accordance with an aspect of the present disclosure.
Figure 9:
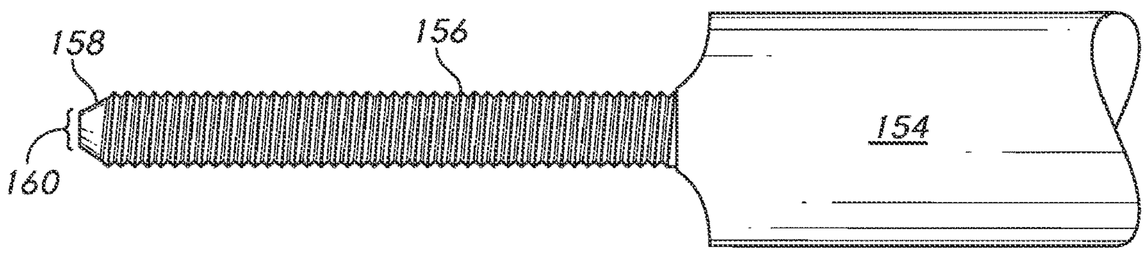
Figure 10:
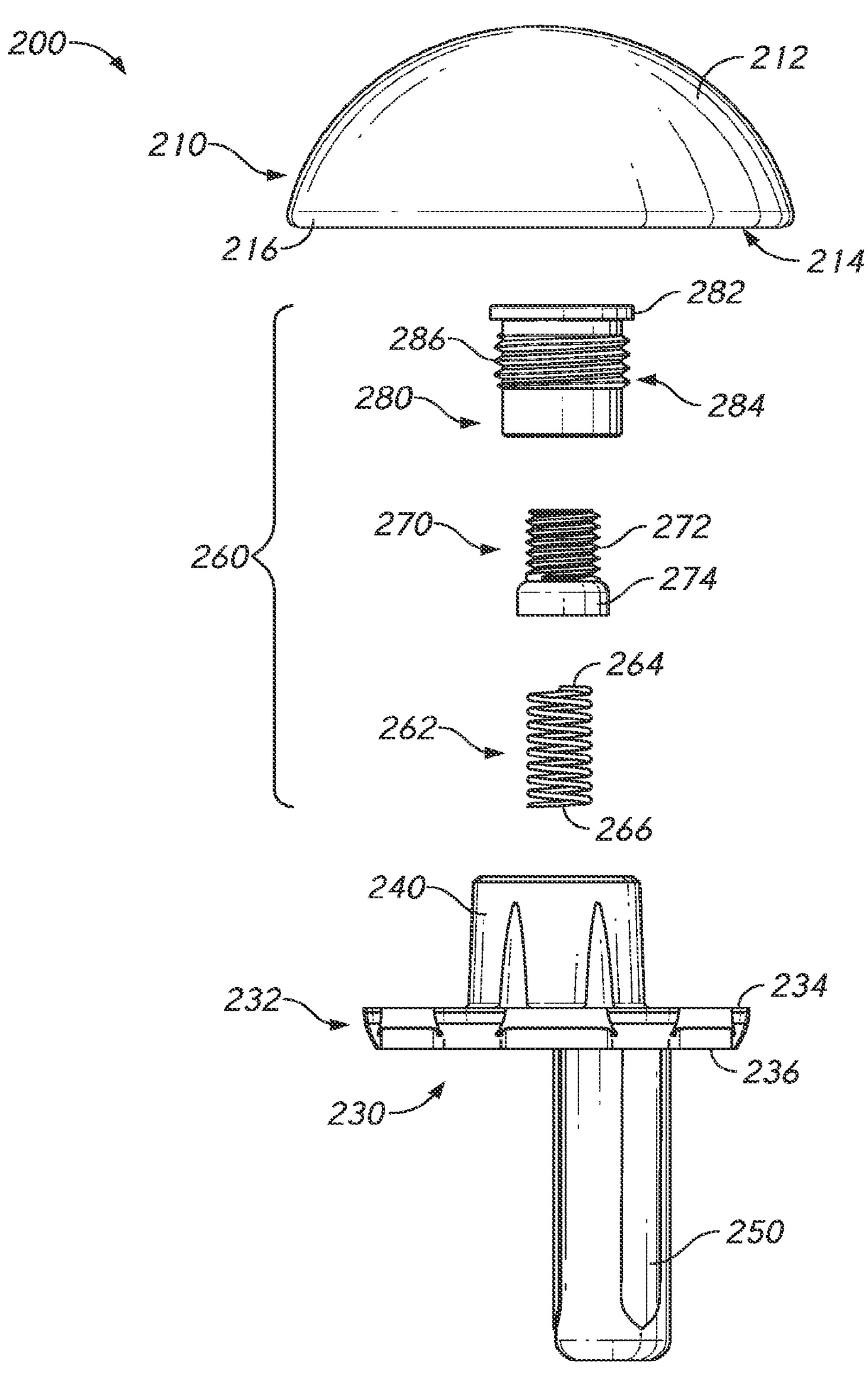
FIG. 10 is an exploded first side view of another implant, in accordance with an aspect of the present disclosure.
Figure 11:
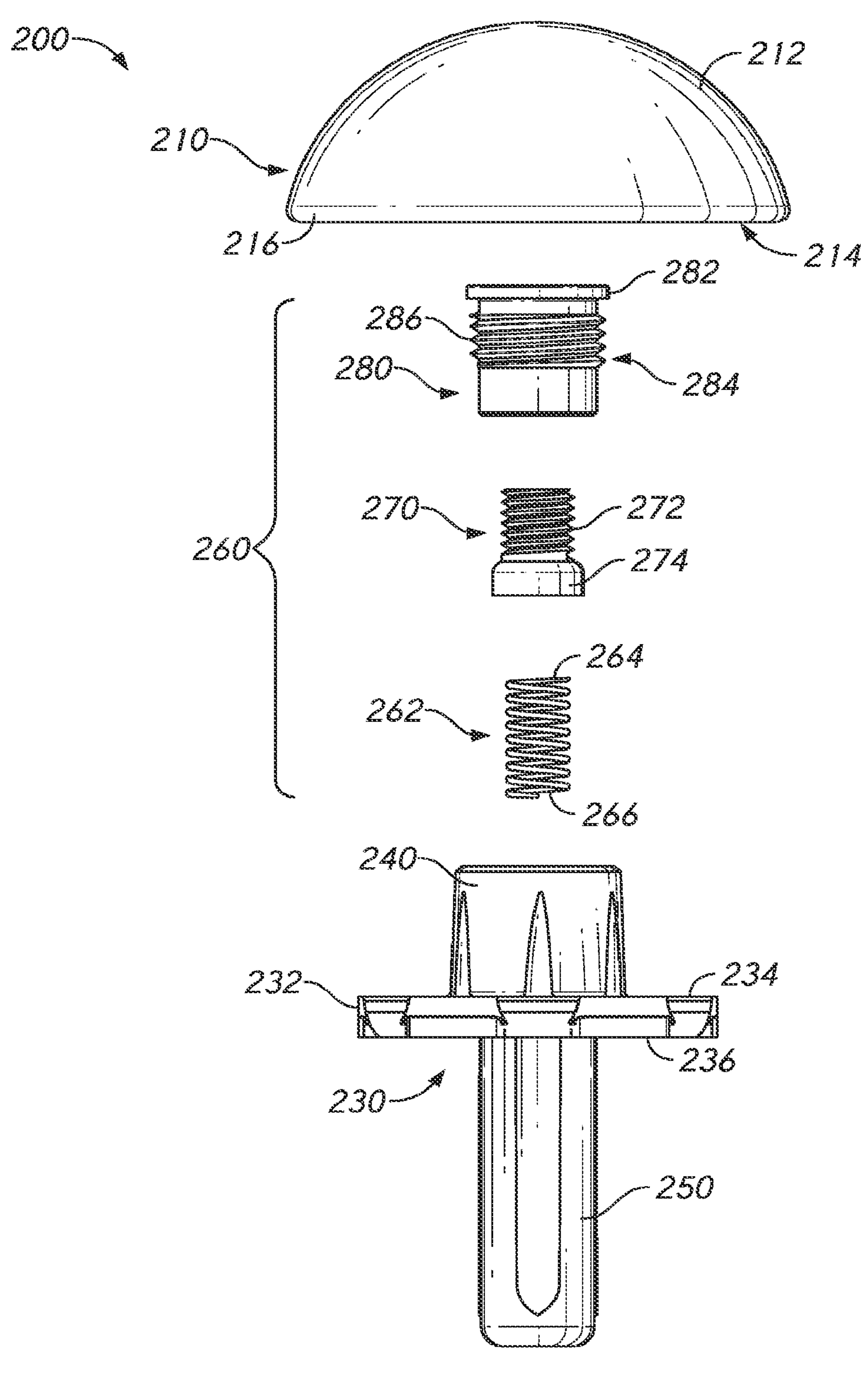
FIG. 11 is an exploded second side view of the implant of FIG. 10, in accordance with an aspect of the present disclosure.

Also disclosed is an extraction device 152, illustrated in FIG. 9, for use with a prosthesis 100 according to any of the embodiments above. The extraction device 152 may include a handle 154, for example, a circular end. The handle 154 may be, for example, a handle for rotating the extraction device 152 or alternatively, a coupling component for engaging a rotating device, such as a drill. Extending from the handle 154 may be a threaded portion 156, for engaging a set of threads 131 in the articulating component 104 of the prosthesis 100. Thus, the threaded portion 156 can be inserted into the through hole 130 of the articulating component 104 by engaging the threads 131 from the convex side 120, opposite the direction of the fixation component 106. Referring now to FIG. 9, the tip 158 of the extraction device 152 may have an engagement projection 160. As seen in FIG. 4, the tip of the fixation component 106 may have an engagement recess 162. The engagement projection 160 may have a cross-sectional shape of, for example, hexagonal, square, or the like to engage the engagement recess 162 of the fixation component to effectively push the fixation component 106 out of the flat side 128 of the articulating component 104 against the force of the spring 138 as the extraction device 152 is rotated. This will allow for the uncoupling of the articulating component 104 from the baseplate 102 via the extraction device 152 without any force being applied against the bone implant interface.

Also disclosed is a method of using a prosthesis 100. For instance, baseplates according to the embodiments above may be positioned within a scapula. Although described as a reverse shoulder replacement, it should be understood that the baseplate can be positioned in the proximal humerus as well, providing an articulating convex surface in its correct anatomic placement. Next, an articulating component as in the above embodiments can be attached to the baseplate, using a hole extending from a first side of the articulating component to a second side of the articulating component, and threaded to receive a fixation component contained within the baseplate.

Referring now to FIGS. 10-18, another implant or prosthesis 200 is shown. The implant 200 may be, for example, a humeral prosthesis or humeral implant. The terms "humeral implant" and "humeral prosthesis," as used herein, shall not be interpreted as limited to use in the humerus, but may also be used for implanting into the glenoid fossa to be utilized in a reverse shoulder configuration, as well as used in other like joints, as would be known by one of ordinary skill in the art. The implant 200 may include an articulating member or component 210, a base member or portion 230, and a coupling portion 260 for connecting the articulating member 210 to the base member 230.

Figure 12:
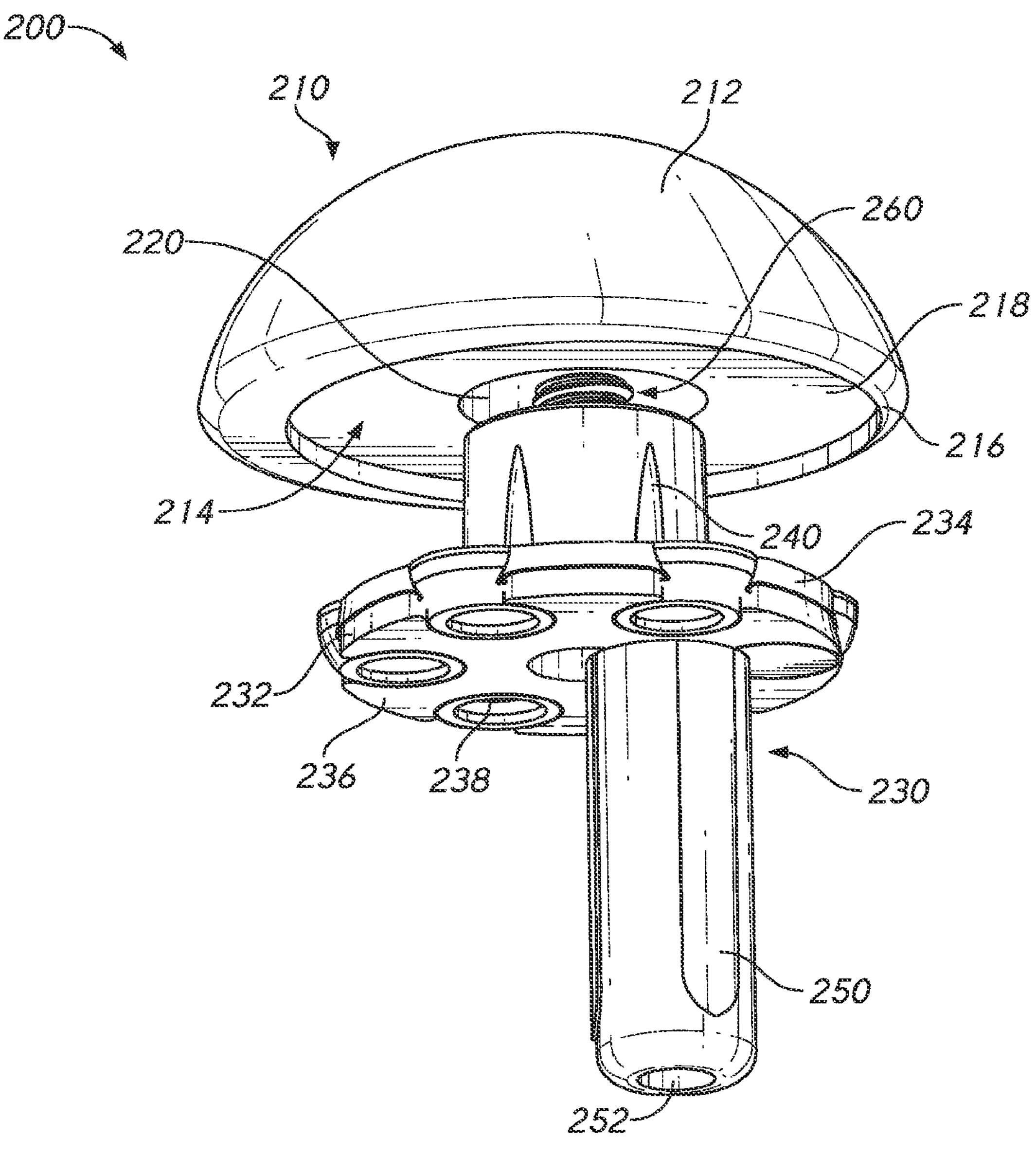
FIG. 12 is a partially exploded first end perspective view of the implant of FIG. 10, in accordance with an aspect of the present disclosure.
Figure 13:
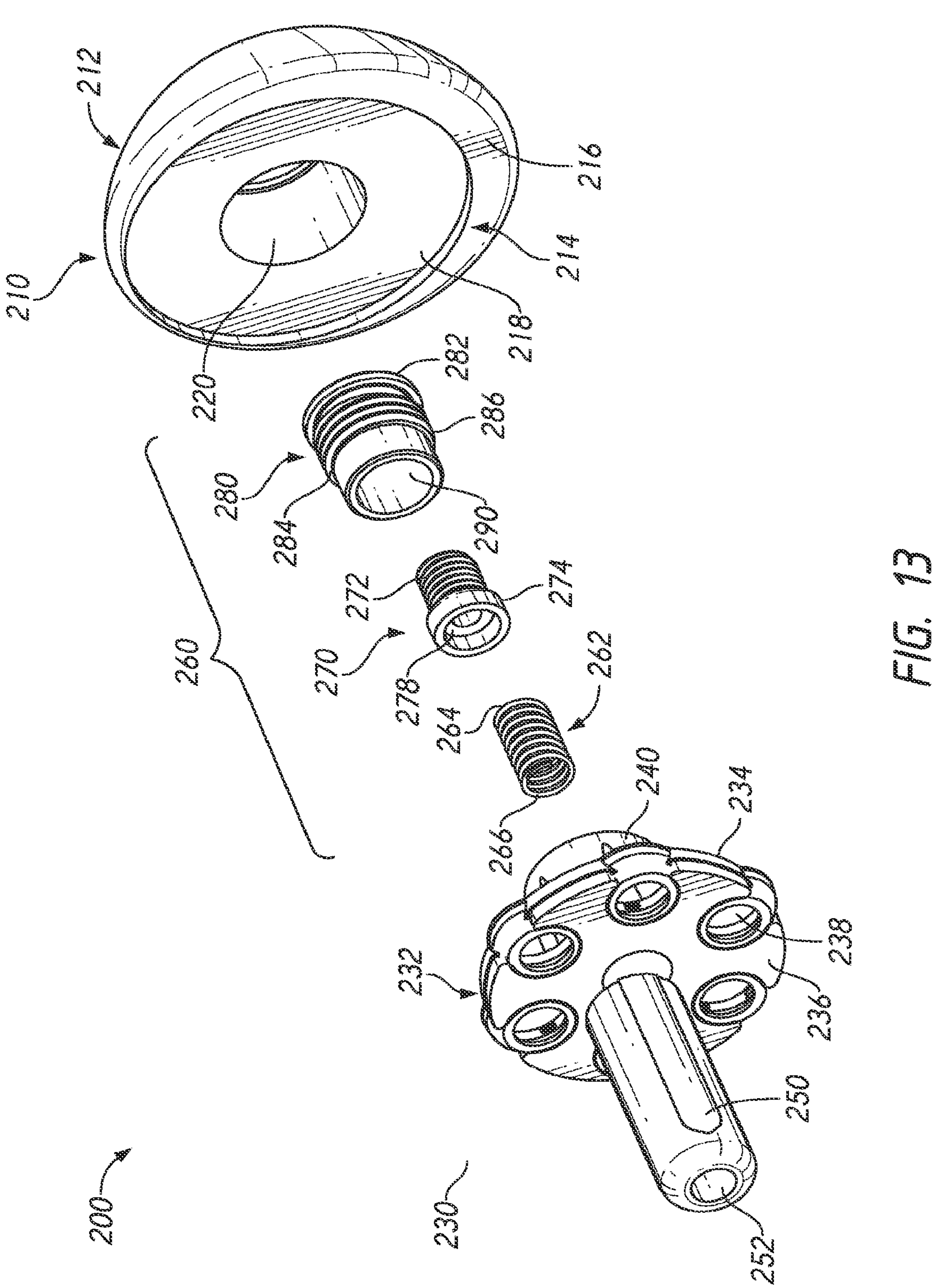
FIG. 13 is an exploded first end perspective view of the implant of FIG. 10, in accordance with an aspect of the present disclosure.
Figure 14:
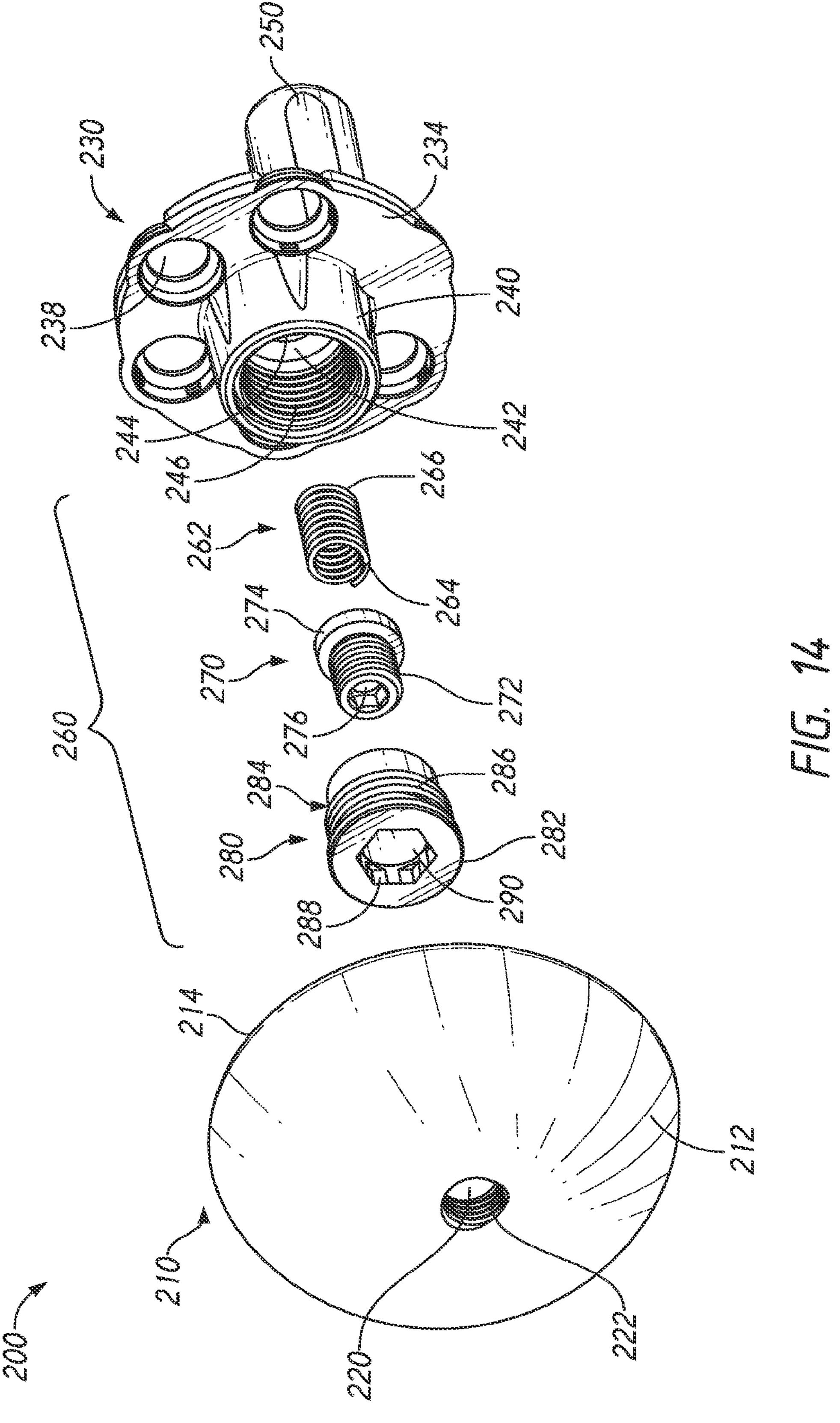
FIG. 14 is an exploded second end perspective view of the implant of FIG. 10, in accordance with an aspect of the present disclosure.
Figure 15:
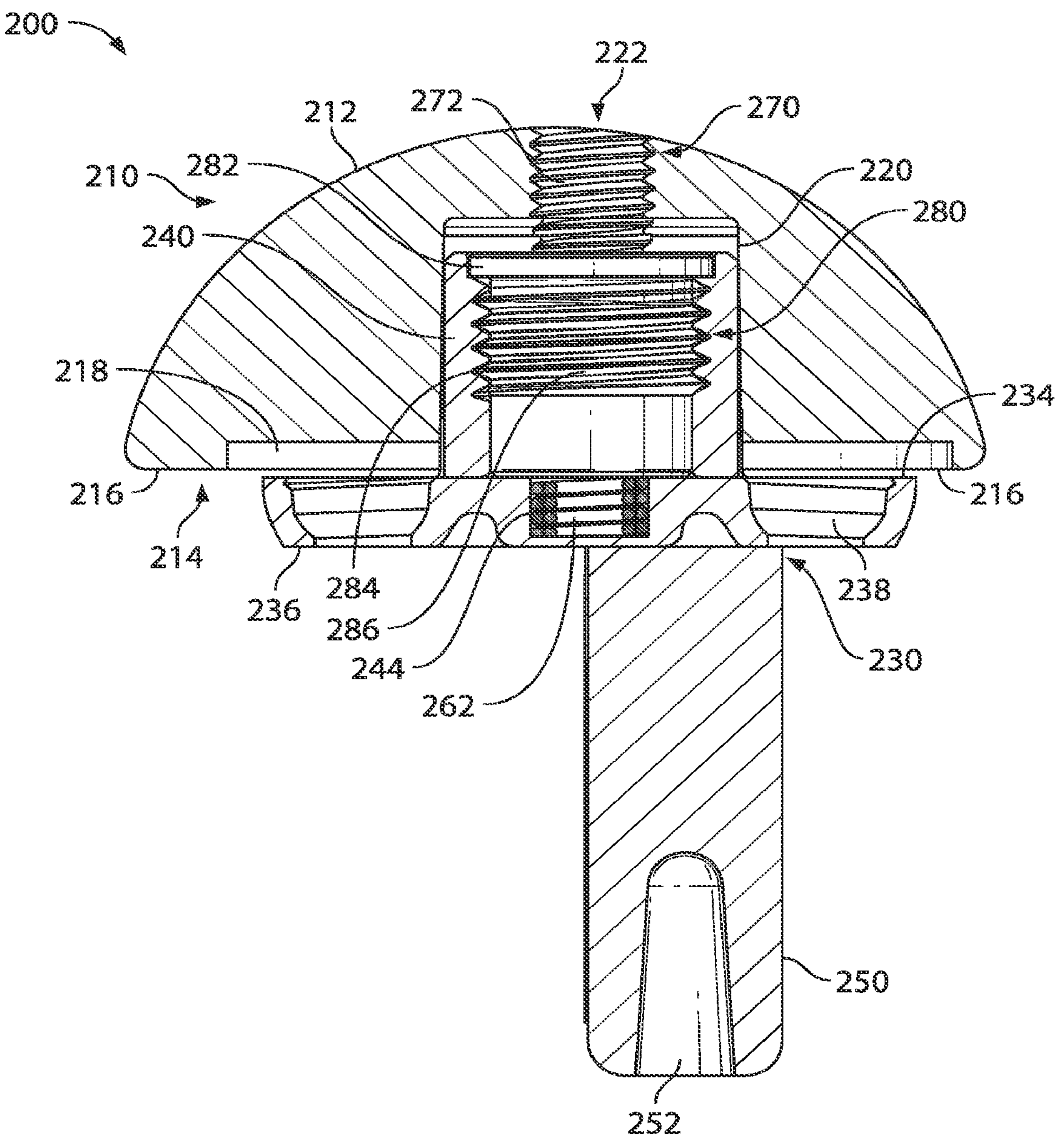
FIG. 15 is an assembled first side view of the implant of FIG. 10 with a transparent articulating member and base member, in accordance with an aspect of the present disclosure.
Figure 16:
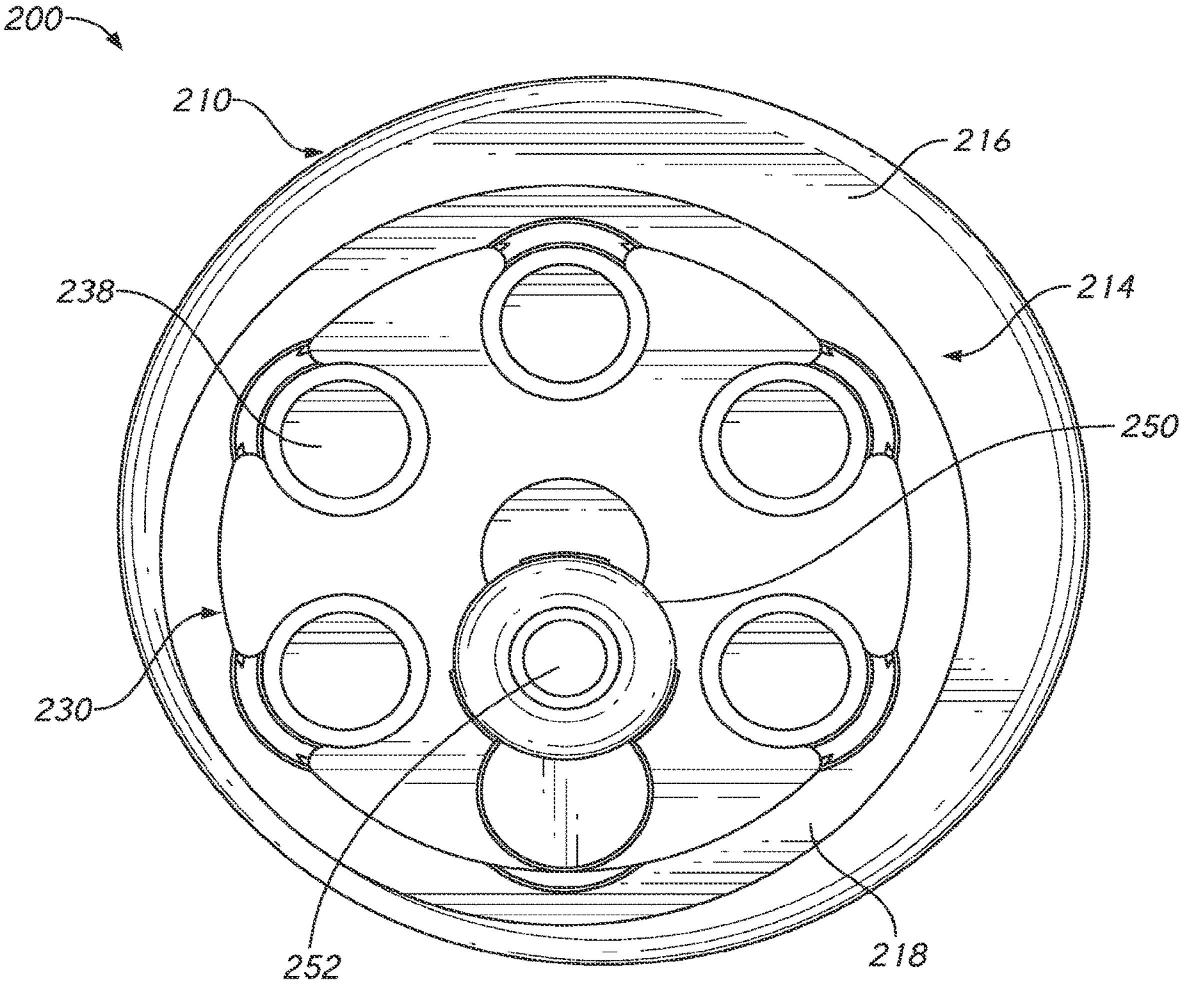
FIG. 16 is a first end view of the implant of FIG. 15, in accordance with an aspect of the present disclosure.
Figure 17:
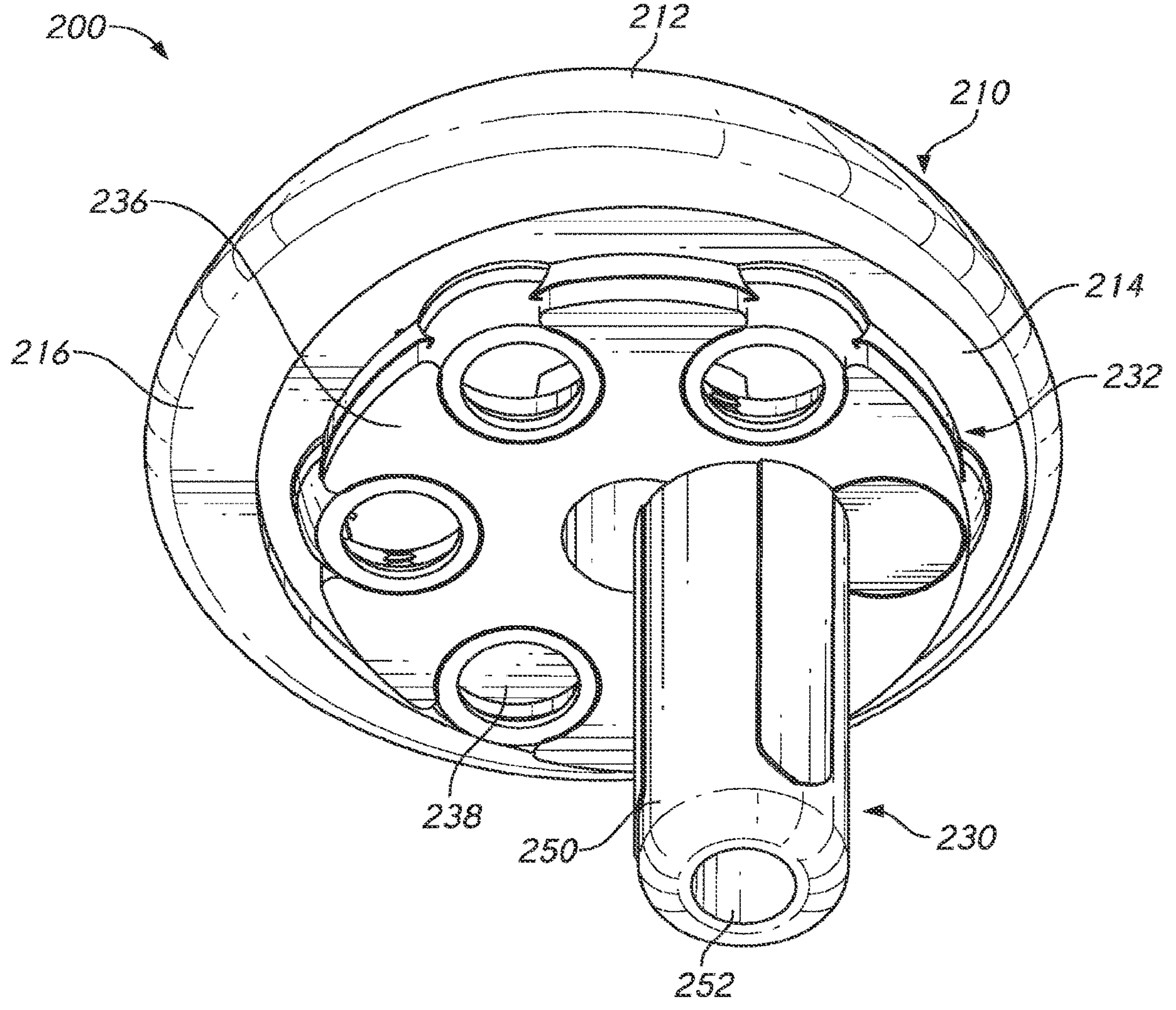
FIG. 17 is a first end perspective view of the implant of FIG. 15, in accordance with an aspect of the present disclosure.
Figure 18:
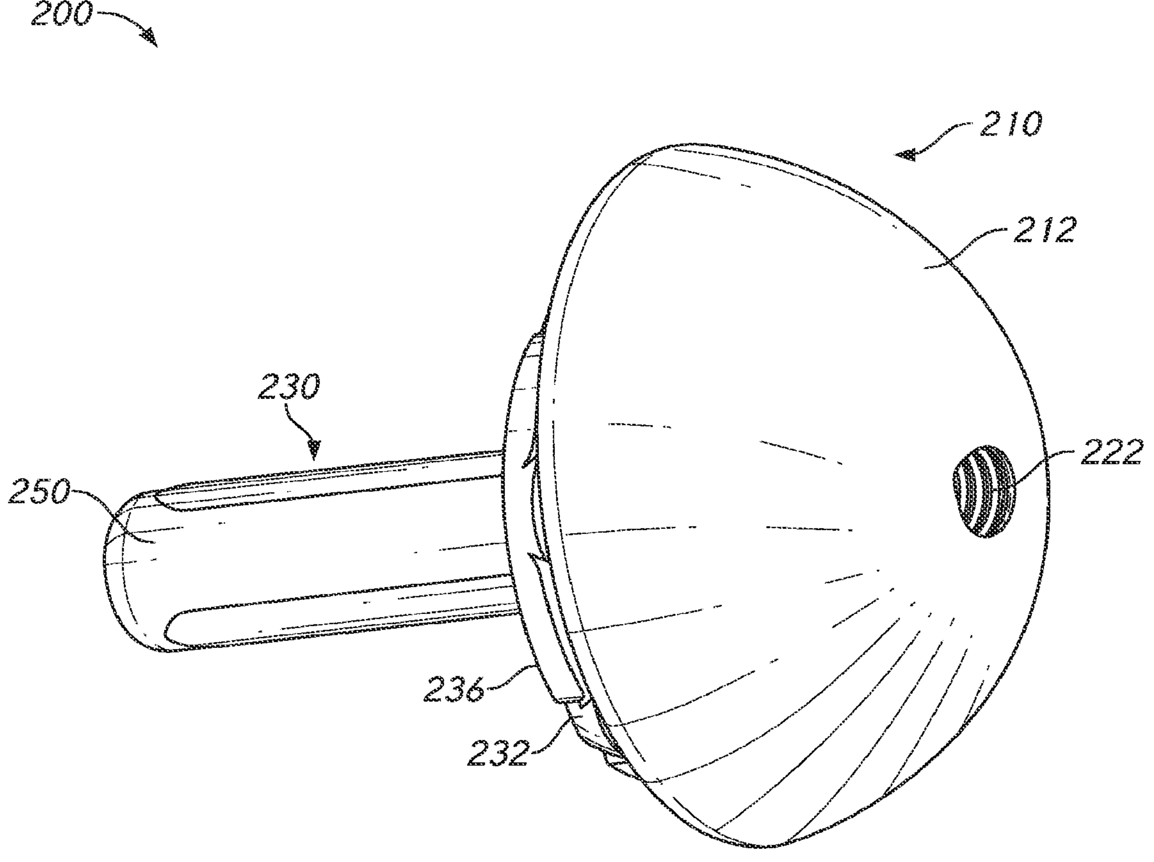
FIG. 18 is a second end perspective view of the implant of FIG. 15, in accordance with an aspect of the present disclosure.

As shown in FIGS. 10-18, the articulating member 210 may include an articulating surface 212 and an interior surface 214. The articulating surface or exterior surface 212 may, for example, have a convex or half spherical shape. The interior surface, flat side, or engagement portion 214 may include an outer lip or lip 216 surrounding the exterior portion of the interior surface 214. The outer lip 216 may include, for example, a width and the width may vary around the circumference of the lip 216. The interior surface 214 may also include a recess 218 positioned within the lip 216 and sized and shaped or configured to receive a portion of the base member 230, as shown in FIGS. 15 and 17. The interior surface 214 may further include a cavity 220 extending into the articulating member 210 from the recess 218 toward the articulating surface 212, as shown in FIGS. 12, 13 and 15. The cavity 220 may extend, for example, through only a portion of the articulating member 210 or, alternatively, from the recess 218 entirely through the articulating surface 212 forming a through hole. The cavity 220 may be, for example, positioned at a center of the articulating member 210, as shown. Alternatively, it is contemplated that the cavity 220 may be positioned, for example, offset from the center, such as, being shifted anteriorly, to allow for building an offset away from the scapula.

With continued reference to FIGS. 10-18, the articulating member 210 may also include a threaded portion or threads 222. The threaded portion or threads 222 may, for example, extend along at least a portion of the interior surface of the cavity 220 or, alternatively, the threaded portion or threads 222 may be positioned adjacent to the cavity 220. For example, as shown in FIG. 15, the threaded portion 222 extends from a bottom of the cavity 220 through the articulating member 210 to the articulating surface 212. The threaded portion 222 may have, for example, a diameter smaller than the diameter of the cavity 220. The cavity 220 and threaded portion 222 may together form a through hole extending from the interior surface 214 through the articulating member 210 to the articulating surface 212, as shown in FIG. 15. The cavity 220 may be, for example, tapered as it extends from the interior surface 214 of the articulating member 210 toward the articulating surface 212. The cavity 220 may have, for example, a height and a first width or diameter at a first end and the height may be larger than the first width.

The base member or base portion 230 is shown in FIGS. 10-18. The base member 230 may include a plate portion 232 with a top surface 234 and a bottom surface 236. The plate portion 232 may also include a plurality of openings or through holes 238 extending through the plate portion 232 from a top surface 234 to the bottom surface 236, as shown in FIGS. 12-17. The base member 230 may also include a projection 240 extending away from the top surface 234 of the plate portion 232, as shown in FIGS. 10-15. The projection 240 may be positioned, for example, generally centered on the top surface 234 of the plate portion 232 with the plurality of openings 238 positioned around the exterior surface of the projection 240, as shown in FIG. 14. The projection 240 may be, for example, tapered as it extends away from the top surface 234 of the base member 230. The projection 240 may have a taper, for example, ranging between approximately 1° to 8°, as the projection 240 extends away from the base member 230. The projection 240 may have, for example, a height and a first width or diameter positioned where the projection 240 couples to the plate portion 232 and the height may be larger than the first diameter. The projection 240 may also include a cavity or opening 242 extending into the projection 240 from a first or top end, as shown in FIGS. 14 and 15. With continued reference to FIGS. 14 and 15, the cavity 242 may further include a recess or spring opening 244 in a bottom surface of the cavity 242. The recess 244 may, for example, extend into the top surface 234 of the plate portion 232, as shown in FIG. 15. The cavity 242 may also include threads 246, for example, along at least a portion of the interior wall of the cavity 242. The threads 246 may extend, for example, between a top of the projection 240 down to a bottom surface of the cavity 242 or along any portion of the interior surface of the cavity 242 between the top of the projection 240 to the bottom surface, as shown in FIGS. 14 and 15.

The base member 230 may further include a stem 250, as shown in FIGS. 10-18. The stem 250 may extend away from the bottom surface 236 of the plate portion 232. The stem 250 may be, for example, offset from the center of the bottom surface 236 of the plate portion 232, as shown in FIGS. 10 and 12-17. Further, the stem 250 may be offset from the projection 240 in at least one direction from the diametric center, as shown in FIGS. 10, 12, 14, and 15. The stem 250 may also, be positioned between two openings 238, as shown in FIGS. 13 and 16. The stem 250 may further include an opening 252 extending from the distal end into the stem 250, as shown in FIGS. 12, 13, and 15-17. As shown in FIG. 15, the opening 252 may be, for example, tapered as the opening 252 extends toward the plate portion 232.

Referring now to FIGS. 10, 11, and 13-15, the coupling portion 260 is shown. The coupling portion 260 includes a spring or elastic member 262, a first fixation component or articulating coupler 270, and a second fixation component or base coupler 280. A first end of the first fixation component 270 receives at least a portion of the spring 262 and a second end of the first fixation component 270 passes through the second fixation component 280, as shown in FIG. 15. At least a portion of the engaged or coupled spring 262 and first fixation component 270 are received within the second fixation component 280. The spring 262 may include a first end 264 for engaging the first fixation component 270 and a second end 266 for engaging the recess 244 in the base member 230, as shown in FIG. 15.

The first fixation component 270 may include a threaded portion 272 at a first end and a stop member or end member 274 at a second end, as shown in FIGS. 10, 11, 13 and 14. The threads of the threaded portion 272 may extend, for example, from the first end to the stop member 274 or, alternatively, from the first end toward the stop member 274 along only a portion of the first fixation component 270, as shown in FIGS. 10, 11, 13 and 14. Referring now to FIG. 14, the first fixation component 270 may also include a drive opening 276. The drive opening 276 may be sized and shaped or configured to receive an instrument or driver for coupling and removing the first fixation component 270 from articulating member 210, as shown in FIG. 15. The drive opening 276 may be, for example, hexagonal, square, Phillips or another multi-lobed configuration for coupling with an instrument. The second end of the first fixation component 270 may include a recess, spring cavity or spring opening 278, as shown in FIG. 13. The recess 278 may be, for example, inset into the stop member 274 of the first fixation component 270. Further, the recess 278 may be sized and shaped or configured to receive the first end 264 of the spring 262, as shown in FIG. 15.

The second fixation component or base coupler 280 is shown in FIGS. 10, 11, and 13-15. The second fixation component 280 may include a head portion 282 at a first end and a body 284 extending away from the head portion 282 to the second end. The body 284 may include threads 286 along at least a portion of the body 284. For example, the threads 286 may extend from the head portion 282 toward the second end on the exterior surface of the second fixation component 280 along only a portion of the body 284, as shown in FIGS. 10, 11, 13 and 14. Alternatively, the threads 286 may extend from the head portion 282 to the second end on the exterior surface of the body 284 of the second fixation component 280. The second fixation component 280 may also include a drive opening 288 on the first end, as shown in FIG. 14, for receiving an instrument or driver. The drive opening 288 may be, for example, hexagonal, square, Phillips or another multi-lobed configuration for coupling with an instrument. The second fixation component 280 may also include an opening or through hole 290 extending from the drive opening 288 at the first end to the second end, as shown in FIG. 13. The opening 290 may be, for example, sized and shaped or configured to receive the first fixation component 270, as shown in FIG. 15. The drive opening 288 may be sized and shaped or configured to allow the threaded portion 272 of the first fixation component 270 to extend out the first end of the second fixation component 280, as shown in FIG. 15. The opening 290 may have, for example, a diameter larger than the width of the drive opening 288 to prevent the stop member 274 of the first fixation component 270 from passing through the interior of the second fixation component 280.

A method of assembling the implant 200 is also disclosed. The method may include inserting the first fixation component 270 into the opening 290 of the second fixation component 280. The method may also include inserting the first end 264 of the spring 262 into the recess 278 of the first fixation component 270 to form the coupling member 260. The method may further include inserting the second end 266 of the spring 262 into the spring opening 244 in the base member 230 and coupling the threads 286 of the body 284 of the second fixation member 280 with the threads 246 in the cavity 242 of the base member 230. This arrangement of the coupling portion 260 creates a biasing force to push the first fixation component 270 out of the second fixation component 280 to be able to engage the articulating component 210. Therefore, after securing the coupling member 260 to the base member 230, at least a part of the threaded portion 272 will extend out of the first end of the second fixation component 280. Optionally, the base member 230 and secured coupling member 260 may be inserted into the patient and then the articulating member 210 may be coupled to the base member 230.

Next, the cavity 220 of the articulating member 210 may be aligned over the projection 240 of the base member 230. Once aligned, the articulating member 210 may be coupled to the base member 230 by applying a force to the articulating member 210 to engage the cavity 220 with the projection 240. If necessary, an instrument (not shown) may be used to force the articulating member 210 into place on the base member 230. As the articulating member 210 engages the base member 230, the spring 262 of the coupling member 260 may be compressed. Once the desired position of the articulating member 210 is achieved on the base member 230, the first fixation component 270 may be rotated to thread the threaded portion 272 of the first fixation component 270 into the threads 222 of the articulating member 210. If the base member 230 wasn't already inserted into a patient, once the articulating member 210 and base member 230 are each coupled to the coupling portion 260, the implant 200 may be inserted into a patient.

Also disclosed is a method of using a prosthesis 200. For instance, base member 230 according to the embodiments above may be positioned within a scapula. Although described as a reverse shoulder replacement, it should be understood that the base members 230 can be positioned in the proximal humerus as well, providing an articulating convex surface in its correct anatomic placement. Next, an articulating member 210 as in the above embodiment can be attached to the base member 230, using the projection 240 of the base member 230, cavity 220 of the articulating member 210, and a coupling portion 260 engaging the articulating member 210 and the base member 230, as described in greater detail above with reference to FIGS. 10-18 and which will not be described again here for brevity sake. Once the coupling portion 260 is attached to the base portion 230 and inserted into a patient, the surgeon is able to couple the articulating member 210 to the coupling portion 260 and the base portion 230 without having to find an opening in the articulating member 210 to insert additional screws. The shape and size of the cavity 220 in the articulating member 210 may correspond to the shape and size of the projection 240 of the base member 230 to, for example, assist with preventing malalignment during insertion of the implant.

Referring now to FIGS. 19-24, another implant or prosthesis 300 is shown. The implant 300 may be, for example, a humeral prosthesis or humeral implant. The terms "humeral implant" and "humeral prosthesis," as used herein, shall not be interpreted as limited to use in the humerus, but may also be used for implanting into the glenoid fossa to be utilized in a reverse shoulder configuration, as well as used in other like joints, as would be known by one of ordinary skill in the art. The implant 300 may include an articulating member or component 210, a base member or portion 310, and a coupling portion 340 for connecting the articulating member 210 to the base member 310.

As shown in FIGS. 19-24, the articulating member 210 may be of the type described above with reference to FIGS. 10-18. As described in greater detail above and which will not be described again here for brevity sake, the articulating member 210 may include an articulating surface or exterior surface 212 and an interior surface, flat side, or engagement portion 214 with the outer lip or lip 216, the recess 218, and the cavity 220, as shown in FIGS. 20 and 22-24. The articulating member 210 may also include a threaded portion or threads 222.

Figure 19:
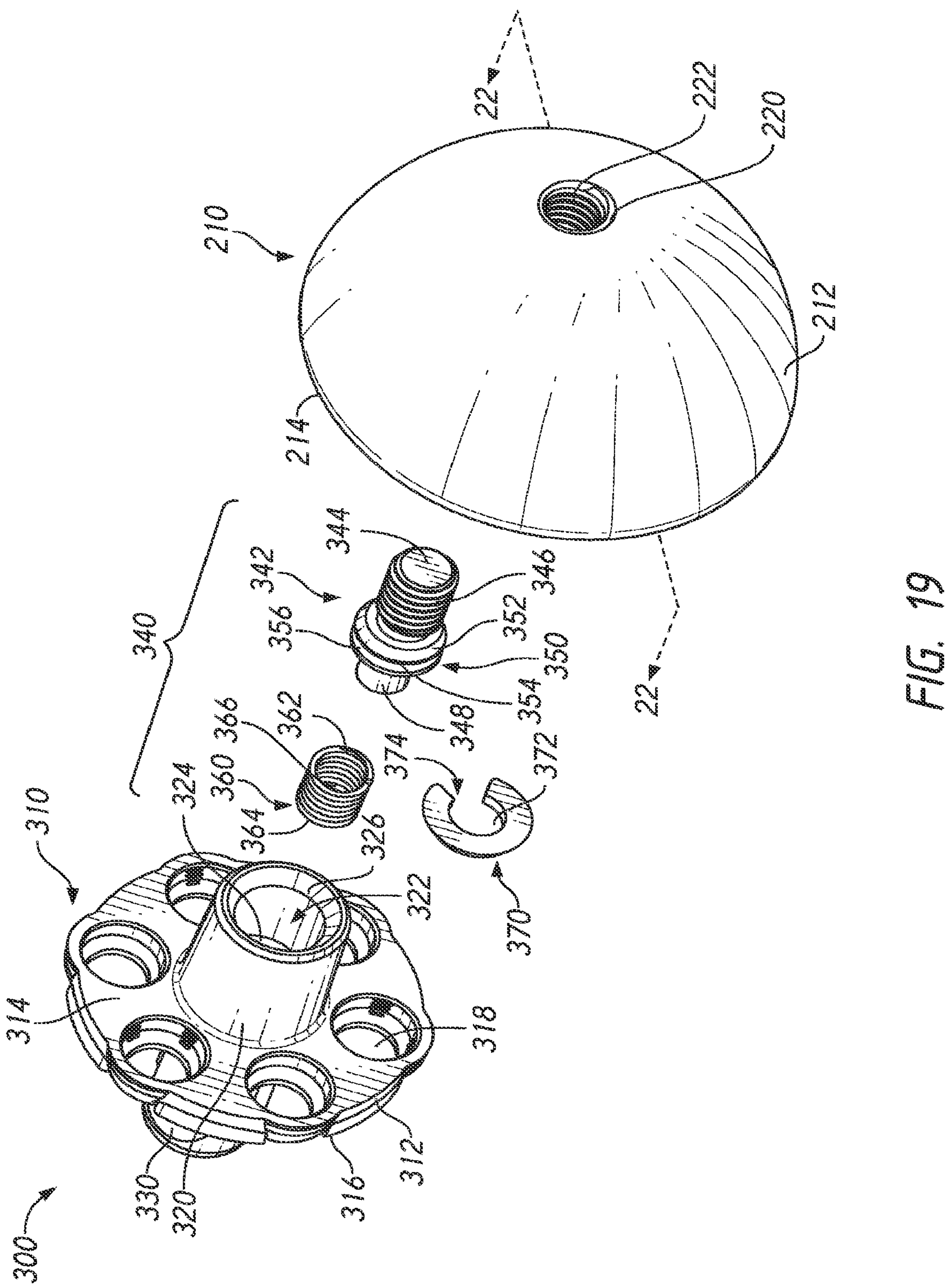
FIG. 19 is an exploded first end perspective view of another implant, in accordance with an aspect of the present disclosure.
Figure 20:
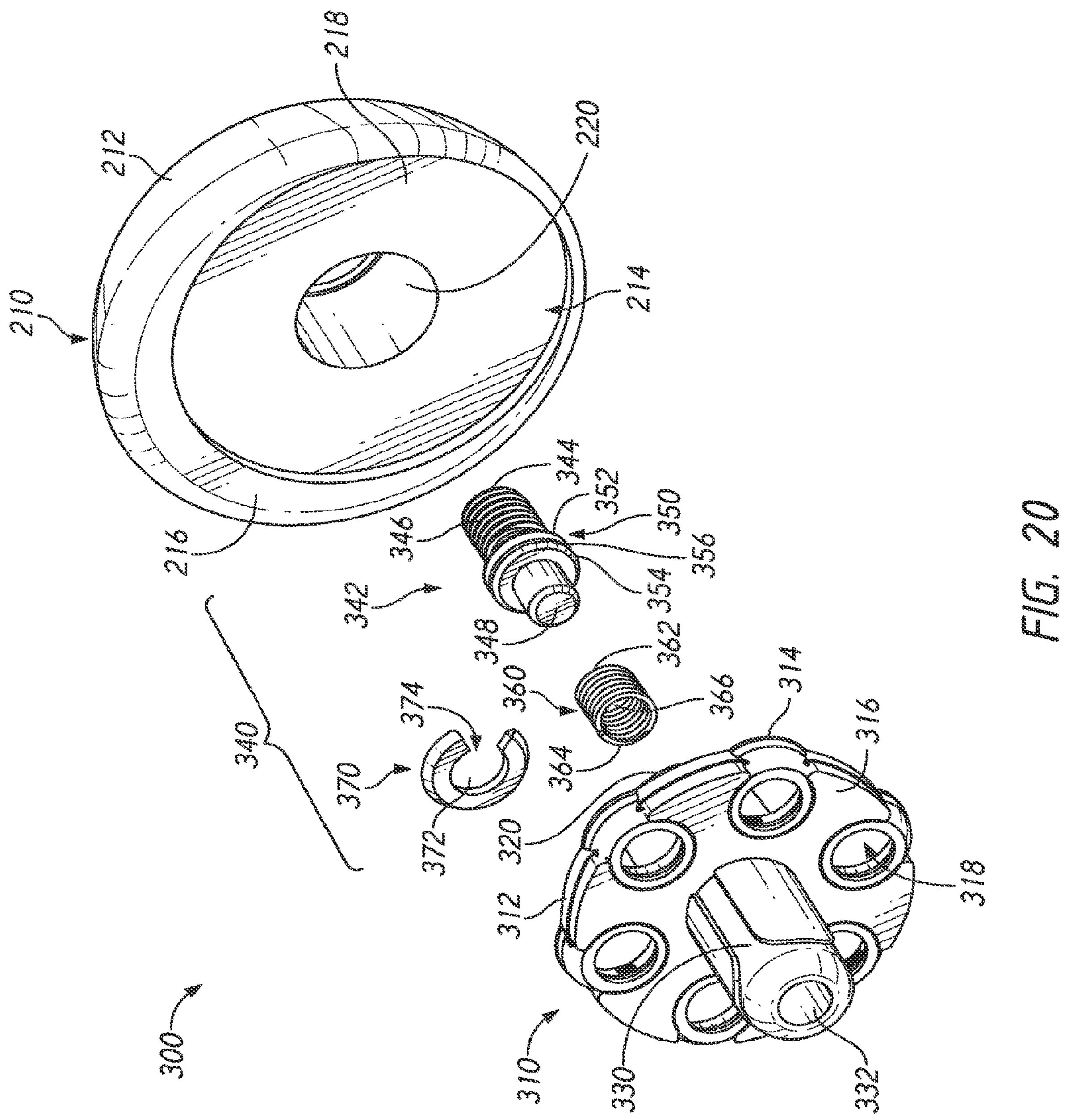
FIG. 20 is an exploded second end perspective view of the implant of FIG. 19, in accordance with an aspect of the present disclosure.
Figure 21:
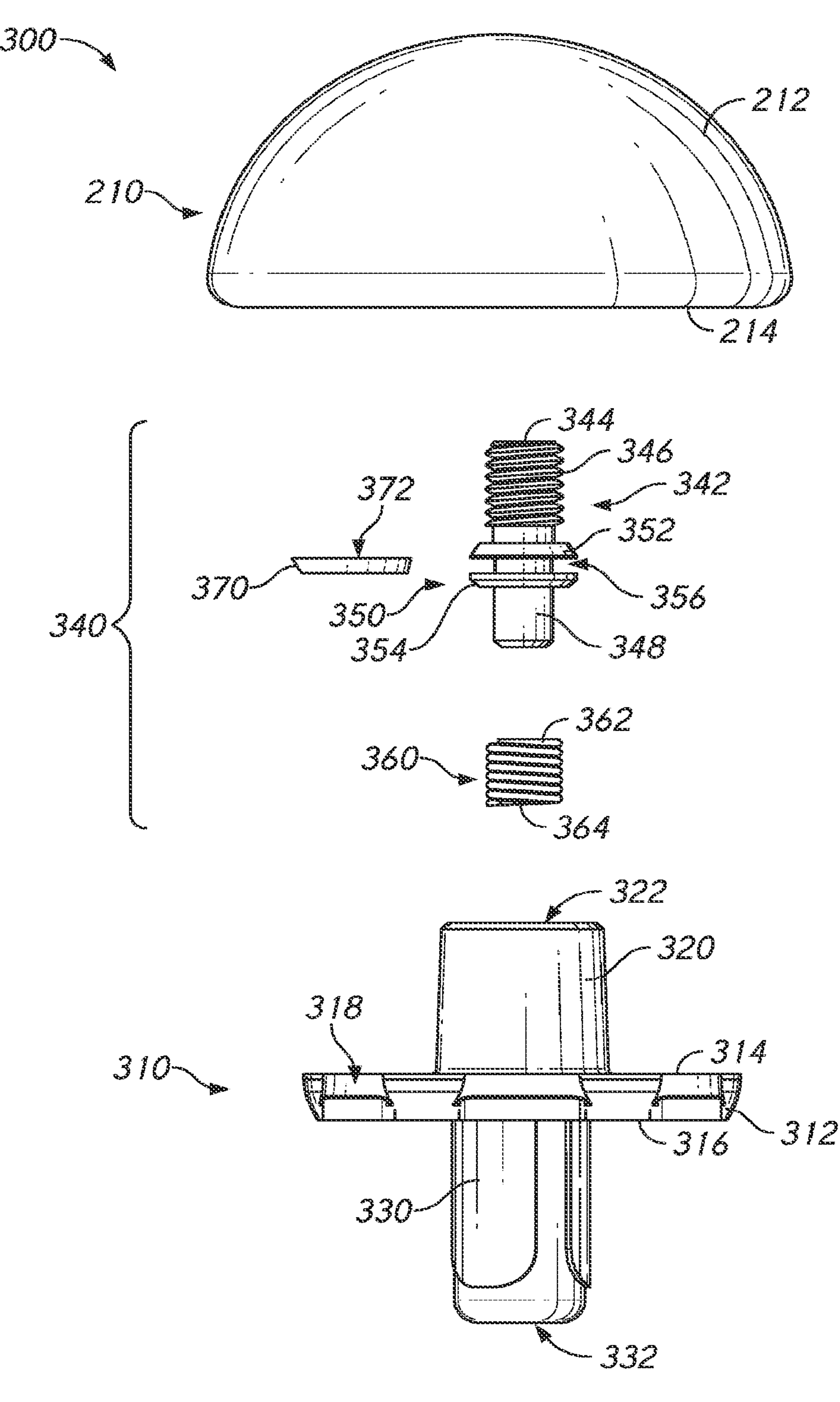
FIG. 21 is an exploded side view of the implant of FIG. 19, in accordance with an aspect of the present disclosure.

The base member or base portion 310 is shown in FIGS. 19-24. The base member 310 may include a plate portion 312 with a top surface 314 and a bottom surface 316. The plate portion 312 may also include a plurality of openings or through holes 318 extending through the plate portion 312 from a top surface 314 to the bottom surface 316, as shown in FIGS. 19, 20, and 22-24. The base member 310 may also include a projection 320 extending away from the top surface 314 of the plate portion 312, as shown in FIGS. 19 and 21-24. The projection 320 may be positioned, for example, generally centered on the top surface 314 of the plate portion 312 with the plurality of openings 318 positioned around the exterior surface of the projection 320, as shown in FIGS. 19 and 20. The projection 320 may be, for example, tapered as it extends away from the top surface 314 of the base member 310. The projection 320 may have a taper, for example, ranging between approximately 1° to 8°, as the projection 320 extends away from the base member 310. The projection 320 may have, for example, a height and a first width or diameter positioned where the projection 320 couples to the plate portion 312 and the height may be larger than the first diameter.

Figure 22:
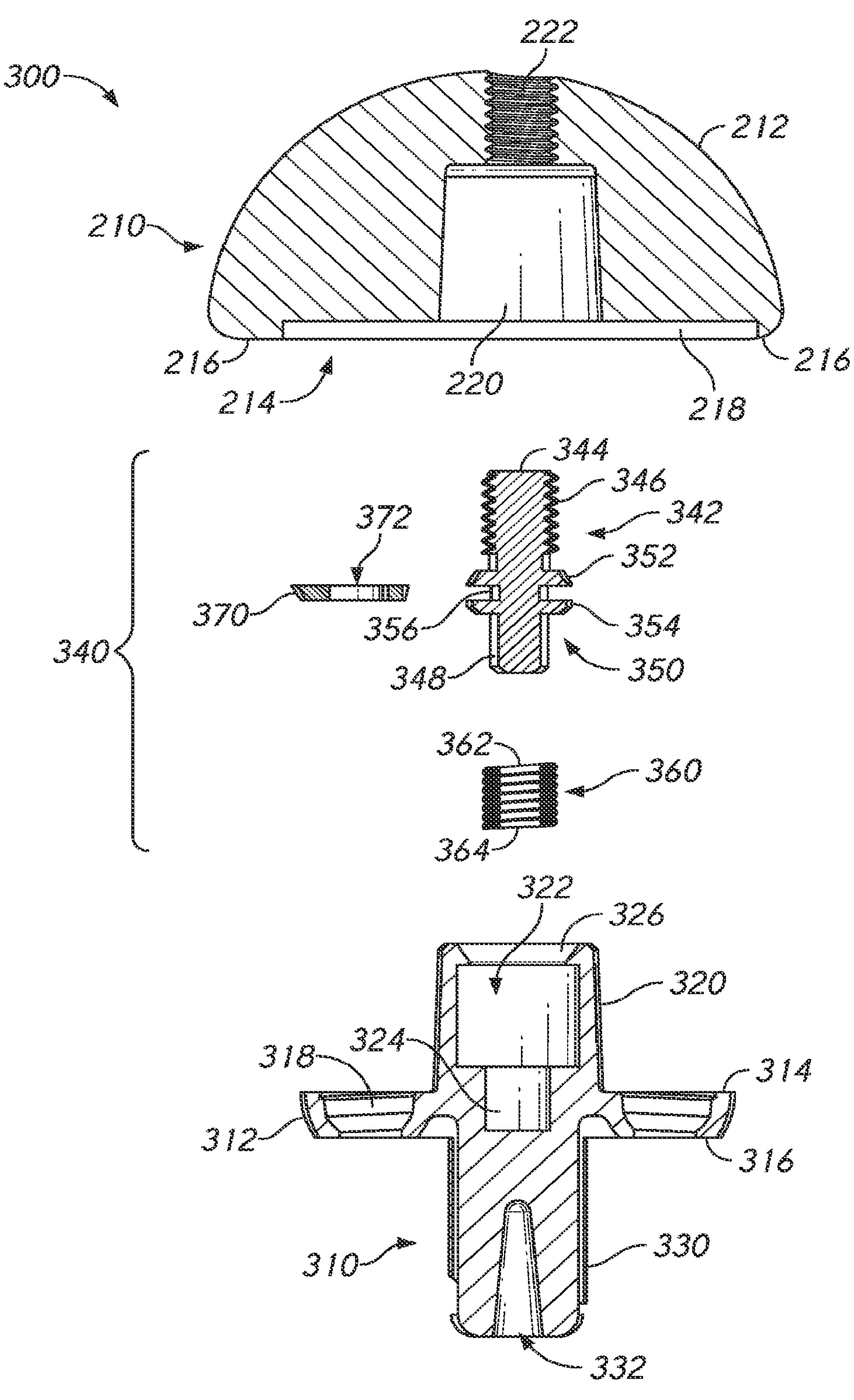
FIG. 22 is an exploded, cross-sectional side view of the implant of FIG. 19 taken along line 22-22, in accordance with an aspect of the present disclosure.
Figure 23:
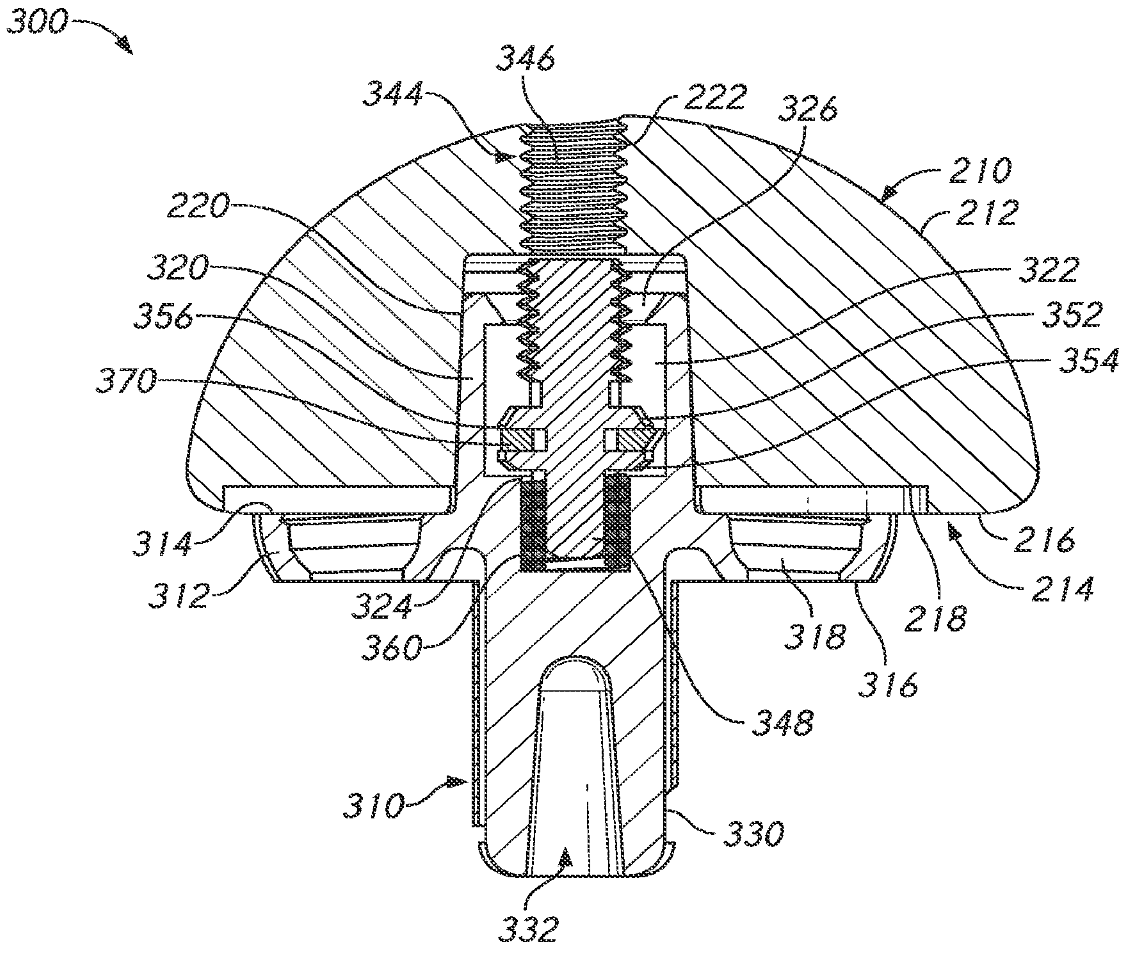
FIG. 23 is an assembled first side view of the implant of FIG. 19 with a transparent articulating member and base member, in accordance with an aspect of the present disclosure.
Figure 24:
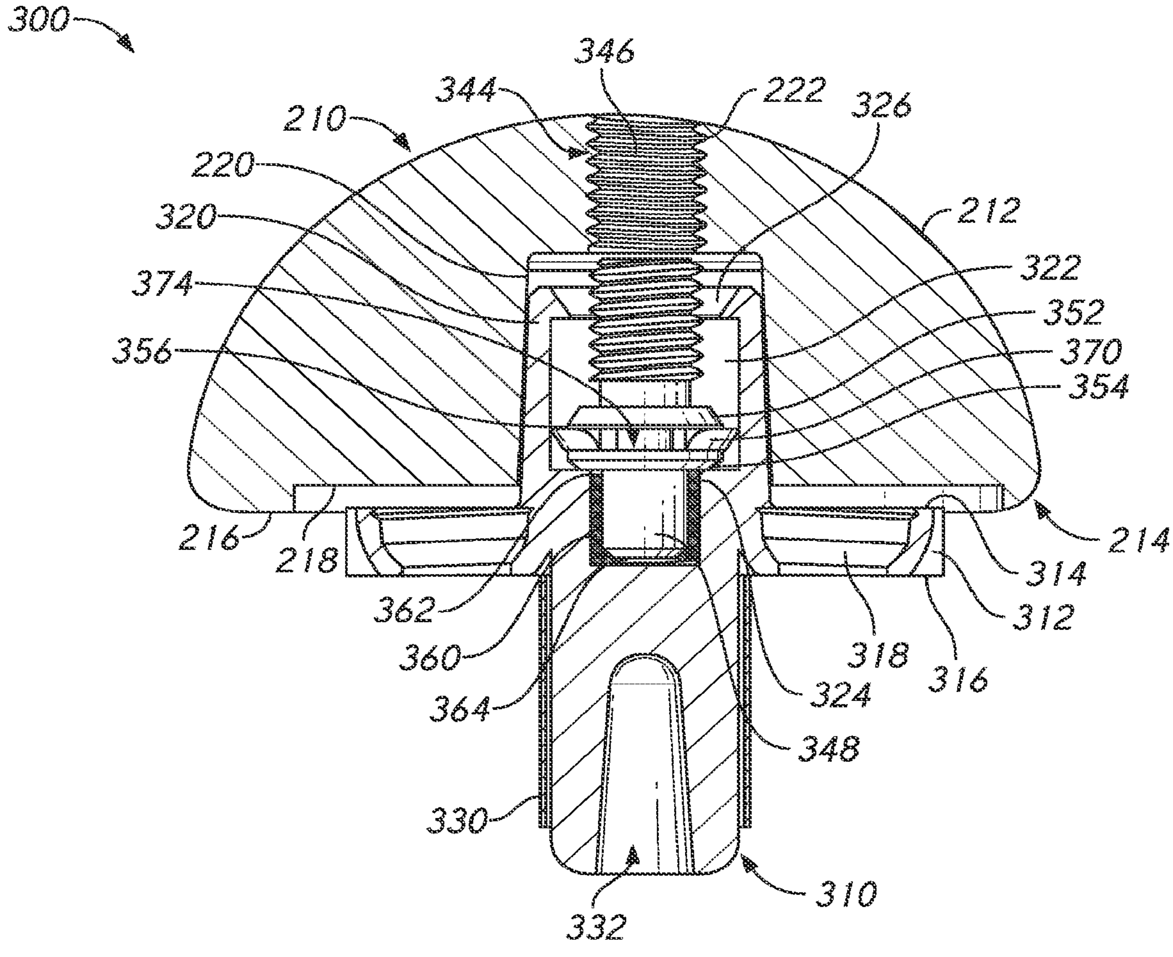
FIG. 24 is an assembled second side view of the implant of FIG. 19 with a transparent articulating member and base member, in accordance with an aspect of the present disclosure.

The projection 320 may also include a cavity or opening 322 extending into the projection 320 from a first or top end, as shown in FIGS. 19 and 22-24. With continued reference to FIGS. 19 and 22-24, the cavity 322 may further include a recess or spring opening 324 in a bottom surface of the cavity 322. The recess 324 may, for example, extend into the top surface 314 of the plate portion 312, as shown in FIGS. 22-24. The cavity 322 may also include a retaining member or rim 326, for example, positioned near a top of the interior wall of the cavity 322. The retaining member 326 may, for example, be chamfered or angled on a top surface and flat or perpendicular to the interior side wall of the cavity 322, as shown in FIG. 22. The opening extending through the retaining member 326 may include a diameter smaller than the diameter of the cavity 322 to engage the coupling portion 340 for securing the articulating member 210 to the base member 310.

The base member 310 may further include a stem 330, as shown in FIGS. 19-24. The stem 330 may extend away from the bottom surface 316 of the plate portion 312. The stem 330 may be, for example, centered on the bottom surface 316 of the plate portion 312, as shown in FIGS. 20-24. Further, the stem 330 may be aligned with the projection 320, as shown in FIGS. 21-24. The stem 330 may also, be positioned centered between all of the openings 318, as shown in FIG. 20. In an alternative embodiment, the stem 330 may be offset as described in greater detail above with respect to stem 250 and which will not be described again here for brevity sake. The stem 330 may further include an opening 332 extending from the distal end into the stem 330, as shown in FIGS. 20 and 22-24. As shown in FIG. 22, the opening 332 may be, for example, tapered as the opening 332 extends toward the plate portion 312.

Referring now to FIGS. 19-24, the coupling portion 340 is shown. The coupling portion 340 includes a securement member or locking bolt 342, a spring or elastic member 360, and an engagement member 370. The securement member 342 may include a first portion 344 positioned at a first end, a second portion 348 positioned at a second end, and an intermediate portion 350 positioned between the first portion 344 and the second portion 348. The first portion 344 may include threads 346 positioned along, for example, at least a section of the first portion 344 between the first end and the intermediate portion 350. The second portion 348 may have a diameter, for example, to receive the spring 360. The intermediate portion 350 may include, for example, a first protrusion 352 extending circumferentially away from the body of the securement member 342 and a second protrusion 354 extending circumferentially away from the body of the securement member 342. The first protrusion 352 may be spaced apart from the second protrusion 354 forming a recess or channel 356 between the protrusions 352, 354. The recess or channel 356 may be, for example, sized to receive the engagement member 370.

Referring now to FIGS. 19 and 20, the engagement member 370 may include a through opening 372 extending from a top surface to a bottom surface of the engagement member 370 and a slot 374 extending from an exterior surface into the opening 372. The engagement member 370 may be, for example, a snap ring, split washer, or the like to be positioned around the body of the securement member 342 and may deform when inserted into the base member 310.

As shown in FIGS. 19-22, the spring 360 may include a first end 362, a second end 364, and a through hole 366 extending from the first end 362 to the second end 364. The through hole 366 of the spring 360 may receive the second portion 348 of the securement member 342, as shown in FIGS. 23 and 24. The first end 362 may engage a bottom surface of the second protrusion 354 and the second end 364 may engage the recess 324 in the base member 310, as shown in FIGS. 23 and 24.

A method of assembling the implant 300 is also disclosed. The method may include forming the coupling member 340. Forming the coupling member 340 may include inserting the second portion 348 of the securement member 342 into the through hole 366 of the spring 360 at the first end 362. Forming the coupling member 340 may also include aligning the slot 374 of the engagement member 370 with the recess 356 in the securement member 342 and inserting the engagement member 370 into the recess 356 of the securement member 342. The method may also include inserting the second portion 348 of the securement member 342 into the cavity 322 in the base member 310. As the second portion 348 is inserted into the cavity 322, the second end 364 of the spring 360 may be inserted into the recess 324 in the base member 310 and the engagement member 370 may be inserted into the cavity 322 past the retaining member 326. As the engagement member 370 is inserted into the cavity 322, the engagement member 370 may deflect to pass the retaining member 326. Once the engagement member 370 passes the retaining member 326, the engagement member 370 will expand to the original size and secure the securement member 342 to the base member 310, as shown in FIGS. 23 and 24. The securement member 342 may translate within the cavity 322 with respect to the force applied to the spring 360 until the engagement member 370 engages the retaining member 326. At least part of the first portion 344 will extend out from the projection 320 of the base member 310 to engage the articulating member 210, as shown in FIGS. 23 and 24. Optionally, the base member 310 and secured coupling member 340 may be inserted into the patient and then the articulating member 210 may be coupled to the base member 310.

Next, the method may include aligning and inserting the projection 320 of the base member 310 into the cavity 220 of the articulating member 210. A force may be applied to the articulating member 210 to engage the cavity 220 with the projection 320. If necessary, an instrument (not shown) may be used to force the articulating member 210 into place on the base member 310. As the articulating member 210 engages the base member 310, the spring 360 of the coupling member 340 may be compressed. Once the desired position of the articulating member 210 is achieved on the base member 310, the first portion 344 of the securement member 342 may be engaged and rotated to couple the threads 346 of the securement member 342 to the threaded portion 222 of the articulating member 210. Although not shown, the first portion 344 may include a driver opening, such as driver opening 276 of implant 200, which will not be described again here for brevity sake. If the base member 310 wasn't already inserted into a patient, once the articulating member 210 is attached to the coupling portion 340 and base member 310, the implant 300 may be inserted into a patient.

Also disclosed is a method of using a prosthesis 300. For instance, a base member 310 according to the embodiment above may be positioned within a scapula. Although described as a reverse shoulder replacement, it should be understood that the base member 310 can be positioned in the proximal humerus as well, providing an articulating convex surface in its correct anatomic placement. Next, an articulating member 210 as in the above embodiments can be attached to the base member 310, using the projection 320 of the base member 310, cavity 220 of the articulating member 210, and the coupling portion 340 engaging the articulating member 210 and the base member 310, as described in greater detail above with reference to FIGS. 19-24 and which will not be described again here for brevity sake. Once the coupling portion 340 is coupled to the base portion 310 and inserted into a patient, the surgeon is able to attach the articulating member 210 to the coupling portion 340 and the base portion 310 without having to find an opening in the articulating member 210 to insert additional screws. The shape and size of the cavity 220 in the articulating member 210 may correspond to the shape and size of the projection 320 of the base member 310 to, for example, assist with preventing malalignment during insertion of the implant.

As may be recognized by those of ordinary skill in the art based on the teachings herein, numerous changes and modifications may be made to the above-described and other embodiments of the present invention without departing from the scope of the invention. The articulating member or spherical shaped articulating component, base member or base plate, coupling portion or fixation component, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component (s) or feature(s) to provide a similar function for the intended purpose. In addition, the devices and systems may include more or fewer components or features than the embodiments as described and illustrated herein. For example, the components and features of FIGS. 1-8, FIGS. 10-18, and FIGS. 19-24 may all be used interchangeably and in alternative combinations as would be modified or altered by one of skill in the art. Accordingly, this detailed description of the currently-preferred embodiments is to be taken in an illustrative, as opposed to limiting of the invention.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An implant, comprising:

a base member configured to be secured in bone, the base member comprising:

a plate portion, a stem extending from the plate portion, the stem being positioned offset from a center of the plate portion, and a projection extending away from a first side of the plate portion;

an articulating member; and a coupling portion for securing the base member to the articulating member, wherein the coupling portion comprises:

a first fixation component;

a second fixation component including an opening for receiving the first fixation component, wherein the first fixation component is configured to be coupled to the articulating member and the second fixation component is configured to be coupled to the base member, and an elastic member with a first end and a second end, wherein the first end of the elastic member is configured to engage a second end of the first fixation component and the second end of the elastic member is configured to engage a recess inside the projection of the base member, wherein the first fixation component is configured to be received within the second fixation component and a portion of the first fixation component is configured to extend out an opening in a first end of the second fixation component.

2. The implant of claim 1, wherein the stem extends away from a second side of the plate portion.

3. The implant of claim 2, wherein the articulating member includes an outer surface, an interior surface, and a cavity extending into the articulating member from the interior surface.

4. The implant of claim 3, wherein the second fixation component is coupled to the projection of the base member, the projection of the base member with the coupled coupling portion is positioned within the cavity of the articulating member, and the first fixation component is coupled to the articulating member.

5. The implant of claim 4, wherein the plate portion is positioned within a lip extending from the interior surface of the articulating member.

6. The implant of claim 5, wherein the lip has a width and the width varies around a periphery of the interior surface of the articulating member.

7. An implant, comprising:

a base member configured to be secured in bone, the base member comprising a plate portion and a stem extending from the plate portion, the stem being positioned offset from a center of the plate portion;

an articulating member including an outer surface, an interior surface, and a cavity extending into the articulating member from the interior surface; and a coupling portion for securing the base member to the articulating member, wherein the coupling portion comprises:

a securement member with a first portion at a first end, a second portion at a second end, and an intermediate portion positioned between the first portion and the second portion;

an elastic member engaging at least a portion of the second portion; and an engagement member coupled to the intermediate portion, wherein the securement member is configured to be coupled to the articulating member and the engagement member is configured to be coupled to the base member, wherein the base member includes a projection extending away from a first side of the plate portion and the stem extending away from a second side of the plate portion.

8. The implant of claim 7, wherein the first portion has threads along at least a portion of the first portion.

9. The implant of claim 7, wherein the intermediate portion comprises:

a first protrusion coupled to a second end of the first portion;

a second protrusion coupled to a first end of the second portion; and a recess between the first protrusion and the second protrusion, wherein the recess receives the elastic member.

10. The implant of claim 9, wherein the projection of the base member comprises:

a cavity extending into the projection from a top surface of the projection toward the first side of the plate portion; and a retaining member positioned around and extending into the cavity near the top surface of the projection.

11. The implant of claim 10, wherein the first protrusion of the intermediate portion engages a bottom surface of the retaining member of the base member.

12. A method of using an implant, comprising:

positioning a base member of the implant within a bone, the base member including a plate portion, a stem extending from the plate portion and being offset from a center of the plate portion, and a projection extending away from a first side of the plate portion;

attaching an articulating member of the implant to the base member with a coupling portion positioned at least partially within a projection of the base member and the projection and a portion of the coupling portion extending into a cavity within the articulating member to engage a threaded portion in the cavity of the articulating member, wherein the coupling portion includes:

a first fixation component, a second fixation component including an opening for receiving the first fixation component, and an elastic member with a first end and a second end, the first end of the elastic member engaging a second end of the first fixation component, and the second end of the elastic member engaging a recess inside the projection of the base member, wherein when the first fixation component is received within the second fixation component, a portion of the first fixation component extends out of the opening of the second fixation component.

* * * * *